US012773193B2

(12) United States Patent
Hollandsworth et al.

(10) Patent No.: US 12,773,193 B2
(45) Date of Patent: Oct. 27, 2026

(54) ORTHOPEDIC INSTRUMENT CONNECTION MECHANISMS AND RELATED ASSEMBLIES AND SYSTEMS

(71) Applicant: MicroPort Orthopedics Holdings Inc., Arlington, TN (US)

(72) Inventors: Michael D. Hollandsworth, Millington, TN (US); Fred W. Bowman, Germantown, TN (US); Michael L. Brooks, Brighton, TN (US)

(73) Assignee: MICROPORT ORTHOPEDIC HOLDINGS, INC., Arlington, TN (US)

( * ) Notice: Subject to any disclaimer, the term of this patent is extended or adjusted under 35 U.S.C. 154(b) by 254 days.

(21) Appl. No.: 18/612,382

(22) Filed: Mar. 21, 2024

(65) Prior Publication Data

US 2025/0000496 A1 Jan. 2, 2025

Related U.S. Application Data

(60) Provisional application No. 63/511,407, filed on Jun. 30, 2023.

(51) Int. Cl.
*A61B 17/00* (2006.01)

(52) U.S. Cl.
CPC .... *A61B 17/00* (2013.01); *A61B 2017/00464* (2013.01); *A61B 2017/00486* (2013.01)

(58) Field of Classification Search
CPC ... A61B 17/00; A61B 17/162; A61B 17/1604; A61B 17/1659; A61B 17/1668;
(Continued)

(56) References Cited

U.S. PATENT DOCUMENTS

| | | | |
|---|---|---|---|
| 3,866,513 | A | 2/1975 | Hornfeck et al. |
| 4,791,919 | A | 12/1988 | Elloy et al. |

(Continued)

FOREIGN PATENT DOCUMENTS

| | | | |
|---|---|---|---|
| BE | 1015812 | A3 | 9/2005 |
| CN | 201721514342.0 | | 11/2017 |

(Continued)

OTHER PUBLICATIONS

Fourcade, Oliver, European Search Report, Sep. 26, 2024, Munich, Germany.

(Continued)

*Primary Examiner* — Shirley X Jian

(57) ABSTRACT

A medical device connection mechanism, related assemblies and systems comprising generally: a first medical device having: a protrusion, the protrusion including a proximal end and a distal end distally disposed from the proximal end along a height of a body of the protrusion, the body of the protrusion comprising an interrupted threaded portion disposed closer to the distal end than the proximal end; and a second medical device having: an interior sidewall, the interior sidewall defining a hole extending into the second medical device, a discontinuous threaded portion disposed within the hole, the discontinuous threaded portion defining a threadless channel extending along a discontinuous threaded portion height, and the discontinuous threaded portion configured to receive the interrupted threaded portion of the protrusion of the first medical device through the threadless channel.

20 Claims, 13 Drawing Sheets

(58) Field of Classification Search
CPC ..... A61B 17/1675; A61B 17/56; A61B 17/92; A61B 2017/0046; A61B 2017/00464; A61B 2017/00477; A61B 2017/00486; A16B 17/16; A61F 2/2846; A61F 2/4603; A61F 2002/4629
See application file for complete search history.

(56) References Cited

U.S. PATENT DOCUMENTS

| | | | | |
|---|---|---|---|---|
| 6,162,226 | A | 12/2000 | DeCarlo, Jr. et al. | |
| 6,676,706 | B1 | 1/2004 | Mears et al. | |
| 7,531,003 | B2 | 5/2009 | Reindel | |
| 7,867,234 | B2 | 1/2011 | Collazo | |
| 8,597,298 | B2 | 12/2013 | Daniels et al. | |
| 8,932,303 | B2 * | 1/2015 | Bouliane | A61B 17/7082 606/104 |
| 9,011,458 | B2 | 4/2015 | Matyas et al. | |
| 9,095,356 | B2 | 8/2015 | Thomas et al. | |
| 9,149,282 | B2 | 10/2015 | Servidio et al. | |
| 9,232,950 | B2 | 1/2016 | Chaney et al. | |
| 9,339,278 | B2 | 5/2016 | Meridew et al. | |
| 9,386,999 | B2 | 7/2016 | Robertson et al. | |
| 9,554,810 | B2 | 1/2017 | Tsukayama et al. | |
| 9,597,188 | B2 | 3/2017 | Satterthwaite et al. | |
| 9,907,582 | B1 * | 3/2018 | Olea | A61B 17/7002 |
| 10,188,404 | B2 | 1/2019 | Dees et al. | |
| 10,213,215 | B2 | 2/2019 | Servidio et al. | |
| 10,543,005 | B2 | 1/2020 | Dees et al. | |
| 10,898,233 | B2 * | 1/2021 | Jackson | A61B 17/7032 |
| 10,898,240 | B2 * | 1/2021 | Garcia-Bengochea | A61B 17/7089 |
| 10,945,862 | B2 | 3/2021 | Roby et al. | |
| 11,039,939 | B2 | 6/2021 | Zimmerman et al. | |
| 11,331,134 | B2 | 5/2022 | Jones et al. | |
| 11,497,620 | B2 | 11/2022 | Wolfson et al. | |
| 2003/0078669 | A1 | 4/2003 | Martin et al. | |
| 2006/0079898 | A1 * | 4/2006 | Ainsworth | A61B 17/025 606/247 |
| 2007/0168036 | A1 * | 7/2007 | Ainsworth | A61B 17/025 623/17.13 |
| 2009/0005814 | A1 * | 1/2009 | Miller | A61B 17/7085 606/301 |
| 2009/0138053 | A1 * | 5/2009 | Assell | A61F 2/4611 606/301 |
| 2013/0172892 | A1 | 7/2013 | Servidio et al. | |
| 2013/0282019 | A1 * | 10/2013 | Bouliane | A61B 17/888 606/104 |
| 2014/0081410 | A1 | 3/2014 | Lieberman et al. | |
| 2014/0276842 | A1 | 9/2014 | Chernosky et al. | |
| 2014/0276850 | A1 * | 9/2014 | Chaney | A61F 2/461 606/84 |
| 2017/0311988 | A1 * | 11/2017 | Petit | A61B 17/7038 |
| 2018/0140336 | A1 * | 5/2018 | Garcia-Bengochea | A61B 17/7005 |
| 2018/0338786 | A1 | 11/2018 | Champagne et al. | |
| 2019/0192171 | A1 | 6/2019 | Muffoletto et al. | |
| 2021/0196285 | A1 | 7/2021 | Hathaway et al. | |
| 2021/0315656 | A1 * | 10/2021 | Denham | A61B 17/00 |
| 2021/0353436 | A1 | 11/2021 | Yoko et al. | |
| 2022/0296256 | A1 * | 9/2022 | Bibard | A61B 17/92 |
| 2022/0361929 | A1 | 11/2022 | Ivan | |
| 2025/0000496 | A1 * | 1/2025 | Hollandsworth | A61B 17/92 |

FOREIGN PATENT DOCUMENTS

| | | |
|---|---|---|
| CN | 202210579308 | 5/2022 |
| CN | 20211656772.1 | 12/2022 |
| WO | 201618347 | 11/2016 |
| WO | 2017151538 | 9/2017 |

OTHER PUBLICATIONS

Exactech Knee Operational Technique Addendum, Exactech, Inc., 2016.
Exactech Knee Design Rationale, Exactech, Inc., 2017.
TRABECULINK Femoral and Tibial Cones Surgical Technique, Waldemar Link GmbH & Co. KG, Jul. 2020.

* cited by examiner

ORTHOPEDIC INSTRUMENT CONNECTION MECHANISMS AND RELATED ASSEMBLIES AND SYSTEMS

REFERENCE TO RELATED APPLICATION

This application claims the benefit of priority to U.S. Provisional Application No. 63/511,407 filed on Jun. 30, 2023. The disclosure of this related application is hereby incorporated into this disclosure in its entirety.

BACKGROUND OF THE INVENTION

1. Technical Field

The present disclosure relates generally to the field of orthopedic surgery, and more particularly to an orthopedic instrument connection mechanism and related systems and assemblies.

2. Related Art

In many minimally invasive orthopedic surgical procedures, the surgeon uses a variety of tools to prepare and orient endoprosthetic implants. Many such instruments comprise a handle and an adaptor. The adaptor can connect to a variety of broaching, reaming, and placement tools that are selectively employed throughout the procedure. To work effectively and to minimize the time that a patient is under anesthesia, the surgeon typically works with a team of technicians, nurses, and other medical professionals to assemble and prepare the various sterilized surgical instruments prior to use.

Some prior orthopedic medical device connection mechanisms consisted of single points of engagement. While these were generally quick to connect and disconnect, these designs could lead to inaccurate or lose fittings of the instruments. Other designs included delicate and complex spring and pin mechanisms, which could be prone to failure after repeated impaction.

Other prior devices, such as the one disclosed by Dees et. al. in PCT. App. No. PCT/US2016/032346, required the use of a guide rod. Guide rods can restrict alignment possibilities and the installation and adjustment of such guide rods can prolong procedure time.

SUMMARY OF THE INVENTION

The problems of the prior art are solved by exemplary orthopedic medical device connection mechanisms in accordance with the present disclosure. An exemplary orthopedic medical device connection mechanism comprises: a first medical device having: a protrusion, the protrusion including a proximal end and a distal end distally disposed from the proximal end along a height of a protrusion body, the protrusion body comprising an interrupted threaded portion disposed closer to the distal end than the proximal end; and a second medical device having: a body, an interior sidewall, the interior sidewall defining a hole extending into the body, a discontinuous threaded portion disposed within the hole, the discontinuous threaded portion defining a threadless channel extending along a discontinuous threaded portion height, and the discontinuous threaded portion configured to receive the interrupted threaded portion of the protrusion of the first medical device through the threadless channel.

It is contemplated that certain exemplary embodiments described herein may permit quick, accurate, and secure assembly and disassembly of orthopedic instruments, while permitting the connection mechanism components to survive repeated blunt force from impaction instruments.

It is further contemplated that certain exemplary embodiments described herein may permit the use of a variety of modular orthopedic medical device assemblies that can be configured to be assembled and disassembled via an exemplary medical device connection mechanism in accordance with this disclosure.

It is still further contemplated that certain exemplary embodiments described herein may permit the use of fewer manual orthopedic instruments at the time of surgery compared to prior designs that utilized complex connection mechanisms.

It is yet still further contemplated that certain exemplary embodiments described herein may permit the user to use orthopedic medical devices in free form (e.g., without being restricted by guiding instrumentation such as an intramedullary rod).

It is still yet further contemplated that certain exemplary embodiments described herein may permit the use of modular medical devices such as modular broaches, wherein a modular broach component of the modular broach is able to be used with any other modular broach component in a provided supply of such components to thereby better accommodate each patient's unique anatomy while minimizing inventory.

BRIEF DESCRIPTION OF THE DRAWINGS

The foregoing will be apparent from the following more particular description of exemplary embodiments of the disclosure, as illustrated in the accompanying drawings. The drawings are not necessarily to scale, with emphasis instead being placed upon illustrating the disclosed embodiments.

DETAILED DESCRIPTION OF THE PREFERRED EMBODIMENTS

Figure 1:
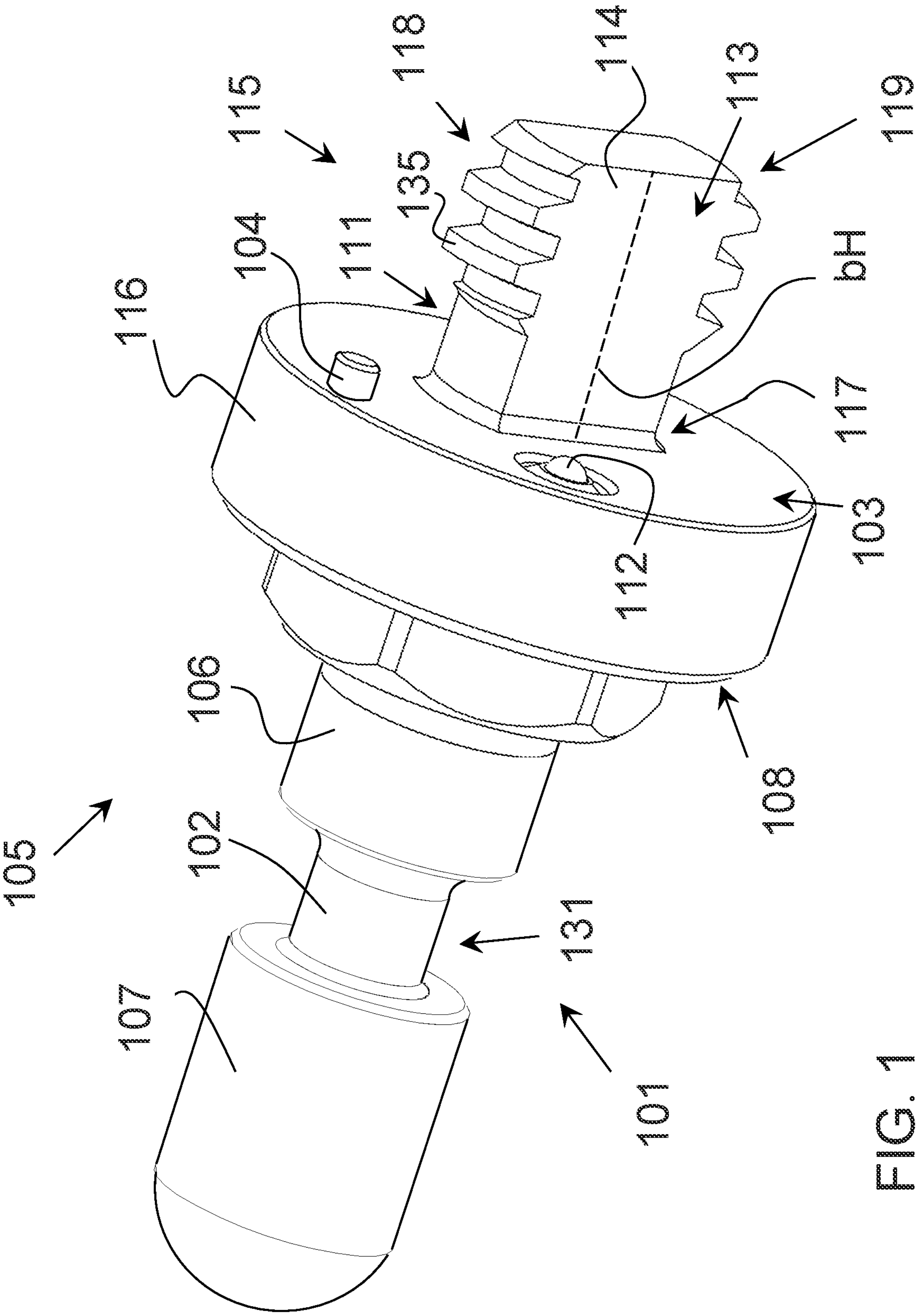
FIG. 1 is an isometric view of an exemplary first medical device, wherein the first medical device is an adaptor of an orthopedic implant assembly.

The following detailed description of the preferred embodiments is presented only for illustrative and descriptive purposes and is not intended to be exhaustive or to limit the scope and spirit of the invention. The embodiments were selected and described to best explain the principles of the invention and its practical application. One of ordinary skill in the art will recognize that many variations can be made to the invention disclosed in this specification without departing from the scope and spirit of the invention.

Similar reference characters indicate corresponding parts throughout the several views unless otherwise stated. Although the drawings represent embodiments of various features and components according to the present disclosure, the drawings are not necessarily to scale and certain features may be exaggerated to better illustrate embodiments of the present disclosure, and such exemplifications are not to be construed as limiting the scope of the present disclosure.

Except as otherwise expressly stated herein, the following rules of interpretation apply to this specification: (a) all words used herein shall be construed to be of such gender or number (singular or plural) as such circumstances require; (b) the singular terms "a," "an," and "the," as used in the specification and the appended claims include plural references unless the context clearly dictates otherwise; (c) the antecedent term "about" applied to a recited range or value denotes an approximation with the deviation in the range or values known or expected in the art from the measurements; (d) the words, "herein," "hereby," "hereto," "hereinbefore," and "hereinafter," and words of similar import, refer to this specification in its entirety and not to any particular paragraph, claim, or other subdivision, unless otherwise specified; (e) descriptive headings are for convenience only and shall not control or affect the meaning of construction of part of the specification; and (f) "or" and "any" are not exclusive and "include" and "including" are not limiting. Further, the terms, "comprising," "having," "including," and "containing" are to be construed as open-ended terms (i.e., meaning "including but not limited to").

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments, whether explicitly described.

To the extent necessary to provide descriptive support, the subject matter and/or text of the appended claims are incorporated herein by reference in their entirety.

Recitation of ranges of values herein are merely intended to serve as a shorthand method of referring individually to each separate value falling within the range of any sub-ranges there between, unless otherwise clearly indicated herein. Each separate value within a recited range is incorporated into the specification or claims as if each separate value were individually recited herein. Where a specific range of values is provided, it is understood that each intervening value, to the tenth or less of the unit of the lower limit between the upper and lower limit of that range and any other stated or intervening value in that stated range of sub range thereof, is included herein unless the context clearly dictates otherwise. All subranges are also included. The upper and lower limits of these smaller ranges are also included therein, subject to any specifically and expressly excluded limit in the stated range.

The terms, "horizontal" and "vertical" are used to indicate direction relative to an absolute reference, i.e., ground level. However, these terms should not be construed to require structure to be absolutely parallel or absolutely perpendicular to each other. For example, a first vertical structure and a second vertical structure are not necessarily parallel to each other.

Throughout this disclosure and unless otherwise noted, various positional terms, such as "distal," "proximal," "medial," "lateral," "anterior," and "posterior," will be used in the customary manner when referring to the human anatomy. More specifically, "distal" refers to the area away from the point of attachment to the body, while "proximal" refers to the area near the point of attachment to the body. For example, the distal femur refers to the portion of the femur near the tibia, whereas the proximal femur refers to the portion of the femur near the hip. The terms, "medial" and "lateral" are also essentially opposites. "Medial" refers to something that is disposed closer to the middle of the body. "Lateral" means that something is disposed closer to the right side or the left side of the body than to the middle of the body. Regarding, "anterior" and "posterior," "anterior" refers to something disposed closer to the front of the body, whereas "posterior" refers to something disposed closer to the rear of the body."

"Varus" and "valgus" are broad terms and include without limitation, rotational movement in a medial and/or lateral direction relative to the knee joint.

The term, "mechanical axis" of the femur refers to an imaginary line drawn from the center of the femoral head to the center of the distal femur at the knee.

The term, "anatomic axis" refers to an imaginary line drawn lengthwise down the middle of femoral shaft or tibial shaft, depending upon use.

Figure 4:
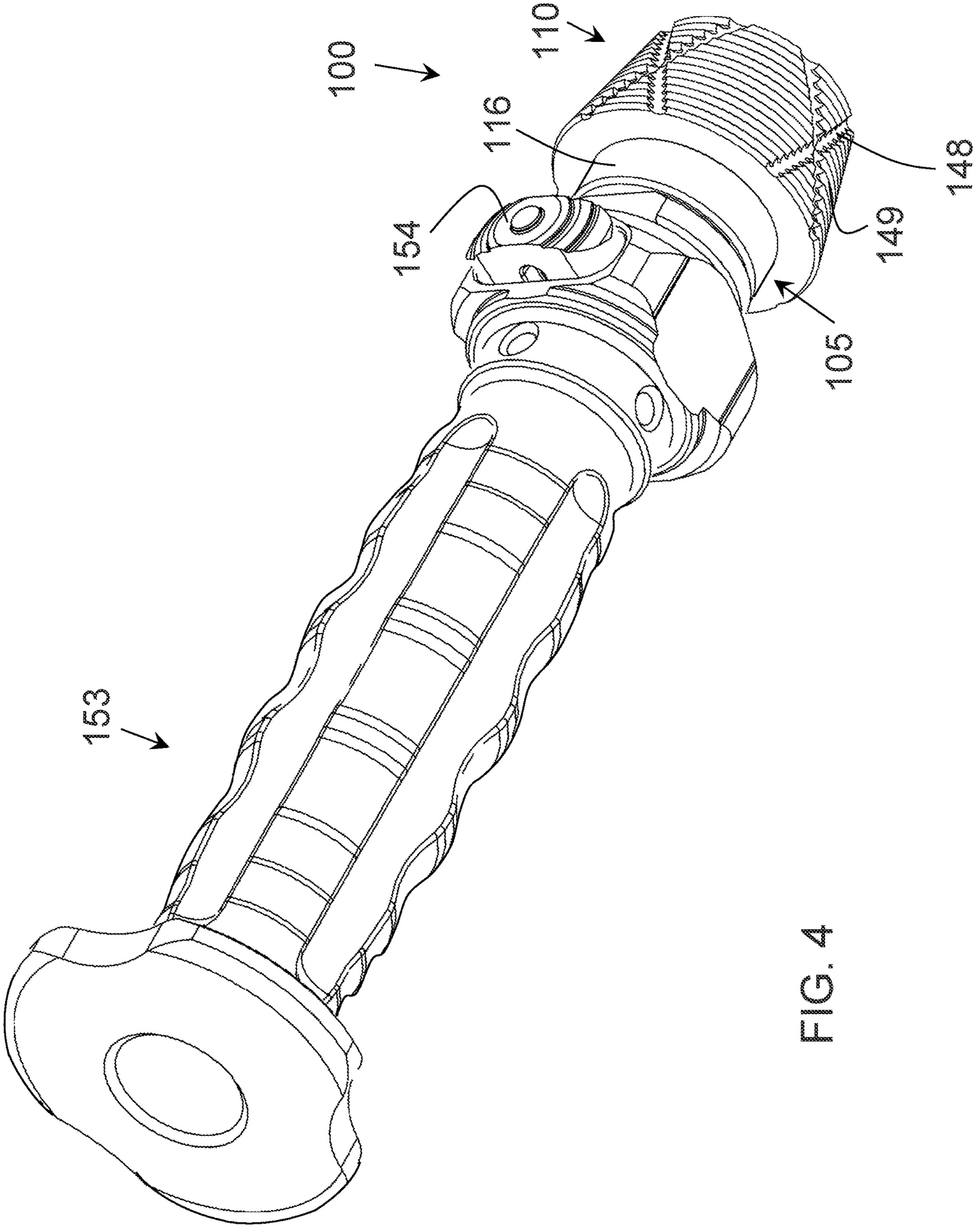
FIG. 4 is an isometric view of an orthopedic instrument assembly having an exemplary medical device connection mechanism and positioner; the orthopedic instrument assembly is depicted in an assembled configuration.
Figure 5:
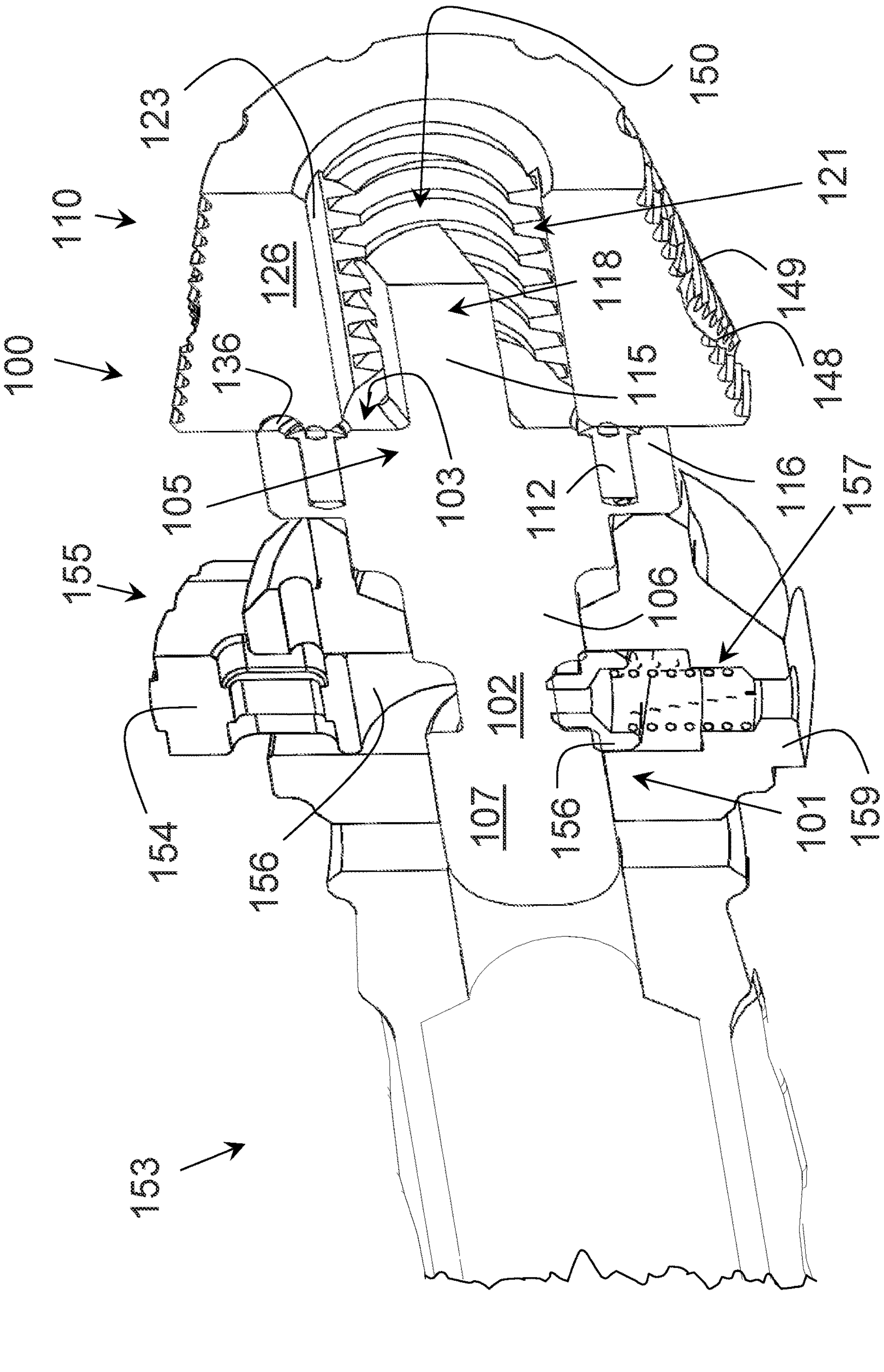
FIG. 5 is a close up perspective cross-sectional side view of the orthopedic instrument assembly of FIG. 4.

FIG. 1 depicts an exemplary first medical device 105 of an orthopedic instrument assembly 100 (FIG. 4) comprising an exemplary medical device connection mechanism 150 (FIG. 5). It will be appreciated that the medical devices disclosed herein are generally contemplated to be used in surgical procedures, particularly in orthopedic surgical procedures. It is contemplated that in certain exemplary embodiments, the medical devices may be orthopedic instruments, orthopedic implants, orthopedic instrument adaptors, combinations or components thereof; however, nothing in this disclosure limits the contemplated "medical devices" to the examples provided. In the depicted exemplary embodiment, the first medical device 105 is an adaptor that comprises a protrusion 115 having a proximal end 117 and a distal end 119 distally disposed from the proximal end 117 along a height bH of a protrusion body 113, the protrusion body 113 can optionally include a shank portion 111 disposed closer to the proximal end 117 than the distal end 119. An interrupted threaded portion 118 is disposed closer to the distal end 119 than the proximal end 117. In other exemplary embodiments, the non-threaded shank portion 111 can be absent and the interrupted threaded portion 118 can extend to the proximal end 117.

The interrupted threaded portion 118 desirably comprises timed screw threads 135 that extend generally radially outward from the non-interrupted portion of the protrusion body 113. In the depicted embodiment, the interrupted portion of the protrusion body 113 comprises two shear faces 114 disposed at opposing sides of the protrusion body 113 and that extend generally along the height bH of the protrusion body 113.

Figure 2:
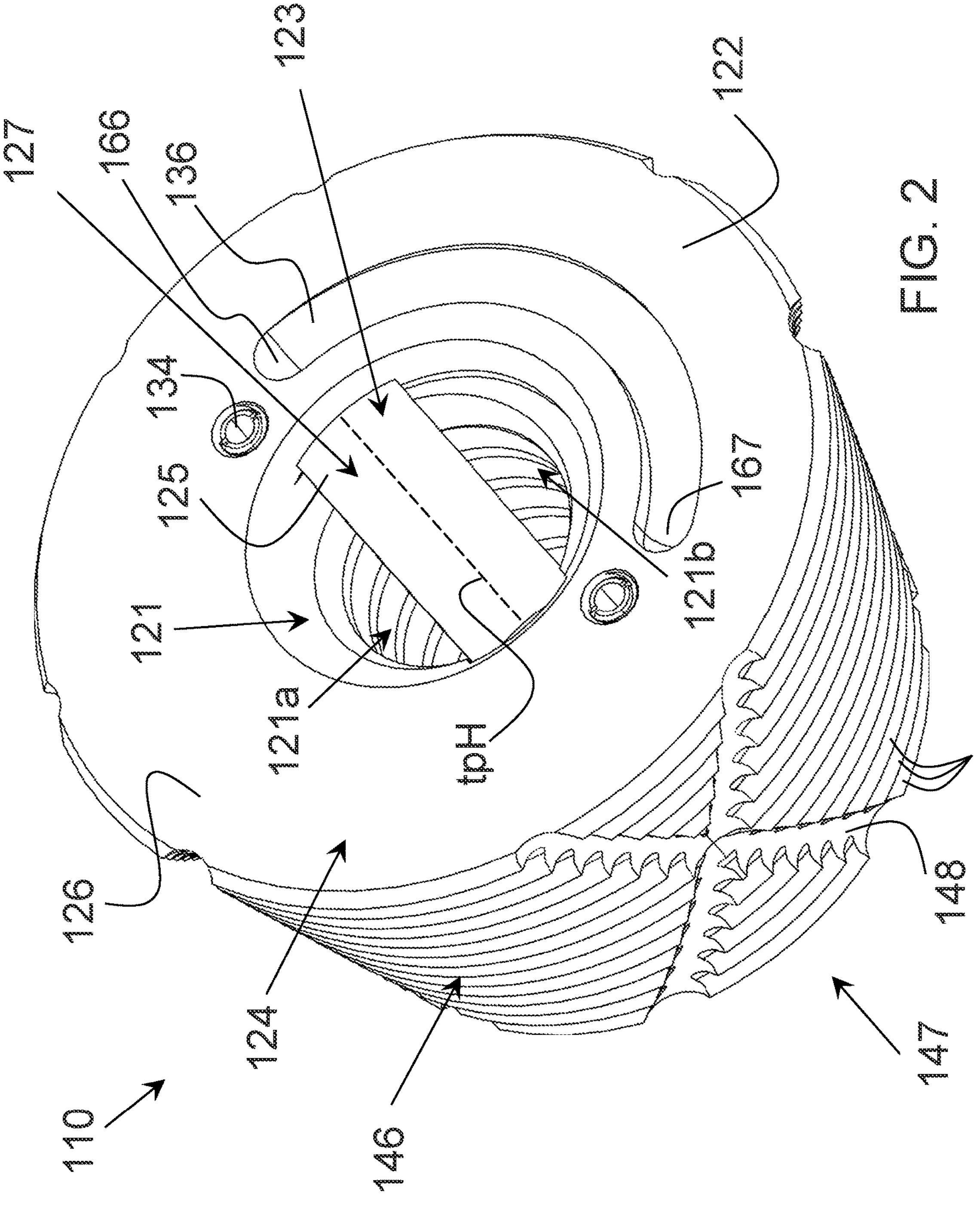
FIG. 2 is an isometric view of an example second medical device, wherein the second medical device is an orthopedic instrument that is configured to receive the adaptor.

FIG. 2 depicts an exemplary second medical device 110 of an orthopedic instrument assembly 100 comprising an exemplary medical device connection mechanism 150. The second medical device 110 comprises a body 126 having a proximal side 124 distally disposed from a distal side 147 and an interior sidewall 129 (FIG. 3) extending between the proximal side 124 and the distal side 147. The interior sidewall 129 defines a hole 127 extending into the body 126 of second medical device 110. A discontinuous threaded portion 121 is disposed within the hole 127. In the depicted embodiment, threads 133 (FIG. 3) of the discontinuous threaded portion 121 extend from the interior sidewall 129 radially inward toward a center longitudinal axis C (FIG. 8A) of the hole 127. The discontinuous threaded portion 121 defines a threadless channel 123 extending along a discontinuous threaded portion height tpH. Stated differently, the absence of screw threads 133 along a portion of the discontinuous threaded portion height tpH defines a threadless channel 123. The distance D between adjacent discontinuous threads 133*a*, 133*b* (FIG. 3) on either side of the threadless channel 123 is desirably sized to closely receive the interrupted threaded portion 118 of the protrusion 115 when the first medical device 105 and the second medical device 110 begin to be engaged (i.e., are disposed in a "pre-engagement" or "preassembled" configuration, sec FIG. 8A). In this manner, the discontinuous threaded portion 121 can be said to be "configured to receive" the interrupted threaded portion 118 of the protrusion 115 of the first medical device 105 through the threadless channel 123. Furthermore, a threadless channel 123 that can closely receive the interrupted threaded portion 118 of the protrusion 115 of the first medical device 105 can be said to be a "keyed slot" or a "keyed threadless channel" 123.

In the depicted embodiments, the distance D between adjacent discontinuous threads 133*a*, 133*b* on either side of the threadless channel 123 is substantially uniform among the multiple adjacent discontinuous threads 133*a*, 133*b*. Without being bound by theory, it is contemplated that this arrangement is desirable because it can facilitate quick guidance of the interrupted threaded portion 118 of the protrusion 115 into the discontinuous threaded portion 121, especially in situations with limited visibility. However, it will be appreciated that this disclosure is not limited to embodiments comprising threadless channels 123 defined by adjacent discontinuous threads 133*a*, 133*b* disposed at a uniform distance D. In certain embodiments, one or more discontinuous threads that are superiorly or inferiorly disposed to a pair of adjacent reference discontinuous threads 133*a*, 133*b* disposed on either side of the threadless channel 123 that are separated by a distance D, can be separated by a threadless channel distance that is greater than or lesser than the distance D of the reference discontinuous threads 133*a*, 133*b*.

Figure 3:
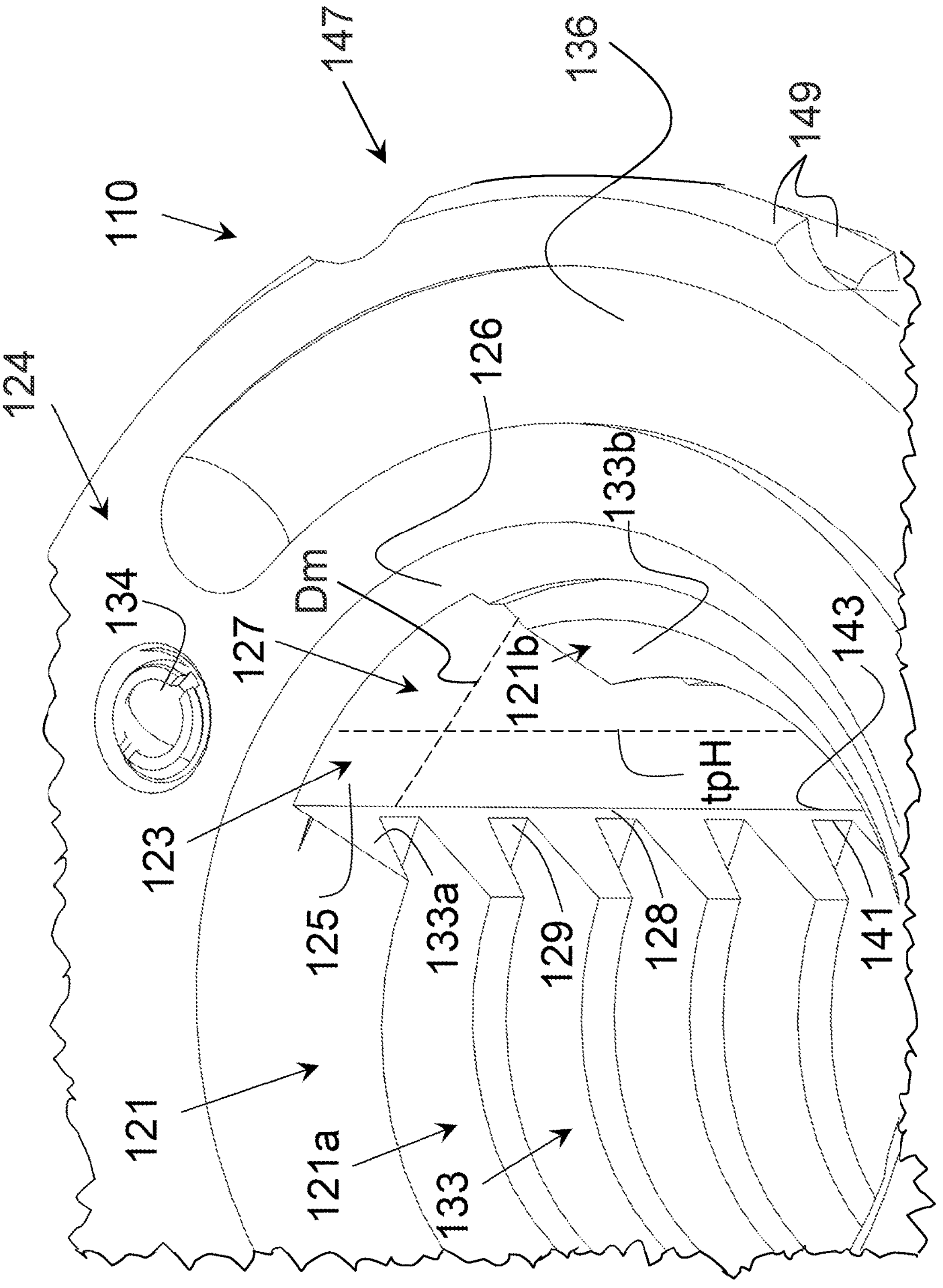
FIG. 3 is a detailed perspective view of the medical device of FIG. 2.

As better seen in FIG. 3, the threadless channel 123 can be recessed into the body 126 of the second medical device 110. Stated another way, the threadless channel interior sidewall 125 is disposed radially outward from the interior sidewall 129. A step 128 extends radially between an edge of 141 of the interior sidewall 129 and an edge 143 of the adjacent threadless channel 123. In this manner, the threadless channel 123 can be said to be "recessed within the body 126 of the second medical device 110." It will be appreciated that that same step and edge structure is typically present on the other side of the threadless channel 123. In the depicted embodiment, a second keyed slot 123*b* is disposed opposite from the first keyed slot (FIG. 2). It will be appreciated that in other exemplary embodiments, the threadless channel interior sidewall 125 can be absent such that the threadless channel 123 further extends radially through the body 126 of the second medical device 110. However, in certain exemplary embodiments, the discontinuous threaded portion 121 can be interrupted by a single keyed slot 123*a*. In other exemplary embodiments, more than two keyed slots can comprise the discontinuous threaded portion 121.

Without being bound by theory, it is further contemplated that a keyed slot 123 that is recessed within the body 126 of the second medical device 110 can further facilitate the alignment and guidance of the interrupted threaded portion 118 of the protrusion 115 of the first medical device 105 when connecting or disconnecting the exemplary connection mechanisms 150 disclosed herein. This is contemplated to be particularly beneficial when visibility is limited. The recessed keyed slot 123 can permit the first medical device 105 to be guided into the second medical device 110 by feel, which can contribute to efficient assembly or disassembly of orthopedic instrument assemblies 100 comprising an exemplary connection mechanism 150.

It will be appreciated that if similar edge 141, 143 and step 128 structures are present in an orthopedic implant, the keyed slot 123 can be said to be "recessed within the body of the orthopedic implant." Similarly, it will be appreciated that if similar edge 141, 143 and step 128 structures are present on a secondary adaptor (see FIG. 10), the keyed slot 123 can be said to be "recessed within the body of the secondary adaptor." In any such embodiment, the opposing steps 128 and the threadless channel interior sidewall 125 can be said to further define the keyed slot 123. The depicted exemplary embodiments comprise two opposing threadless channels 123. As such, the depicted discontinuous threaded portion 121 can be said to comprise a first portion of discontinuous threads 121*a* that is opposed to a second portion of discontinuous threads 121*b*. However, it will be appreciated that in other exemplary embodiments, a single threadless 123 may be present. In yet other exemplary embodiments, more than two threadless channels 123 can be present. In embodiments having multiple threadless channels 123, the threadless channels are desirably disposed at regular intervals relative to the adjacent threadless channel 123 or threadless channels 123. However, it will be appreciated that in other exemplary embodiments, the multiple threadless channels 123 can be disposed at irregular intervals relative to the adjacent threadless channel 123 or threadless channels 123.

In exemplary embodiments, the threads 133 of the discontinuous threaded portion 121 and the threads 135 of the complementary interrupted threaded portion 118 of the protrusion 115 desirably have a trapezoidal cross-section (see FIG. 3) when bisected radially. Without being bound by theory, it is contemplated that screw threads 133, 135 having a trapezoidal cross-section, such as an ACME thread form or a trapezoidal metric thread form, can facilitate increased engagement speed compared to standard threads in part by generally having a lower number of threads per axial distance, having additional strength at the base of the threaded form, and having increased thread shear capacity. It is further contemplated that such trapezoidal threads 133,135, when in cam locking engagement with each other may effectively transfer impaction forces more uniformly through the engaged threads 133, 135 and thereby survive repeated impaction longer compared to non-trapezoidal screw threads. However, nothing in this disclosure limits the screw threads to ACME, trapezoidal metric, or otherwise trapezoidal screw threads. All types of screw threads are considered to be within the scope of this disclosure, including but not limited to standard, V-shaped, American National, Unified, metric, square, ACME, British (Whitworth Standard), knuckle, and buttress type screw threads.

Without being bound by theory, it is contemplated that the threads 133 of the discontinuous threaded portion 121 and the threads 135 of the interrupted threaded portion 118 can desirably be "timed" or "clocked" such that placement of a given orthopedic instrument assembly 100 into the assembled configuration results in a known angular displacement and a known travel depth of the protrusion 115 relative to a starting position of the protrusion 115 (i.e., in the preassembled configuration).

The "thread timing" or "thread clocking" is a function of the pitch and spacing of the thread. In practice, when the threads 135, 133 are placed in the preassembled configuration (see FIG. 8A), the threads 135 of interrupted threaded portion 118 are placed in the threadless channels 123*a*, 123*b* of the discontinuous threaded portion 121. In the embodiment depicted in FIG. 8A, a first transverse axis TA can be imagined to extend between the opposing threadless channels 123*a*, 123*b* and bisect the interrupted threaded portion 118 laterally. When placed in the preassembled configuration, the interrupted threaded portion 118 and the discontinuous threaded portion 121 share a common center longitudinal axis C. With timed threads, the starting point of thread engagement is determined by the thread pitch relative to the shared rotational axis between the internal 135 and external 133 threads and the length of the protrusion 115. As the orthopedic instrument assembly 100 is rotated from the preassembled configuration to the assembled configuration, the threads 135 of the interrupted threaded portion 118 begin to mesh with the threads 133 of the discontinuous threaded portion 121. With timed threads, the length of the protrusion travels a known distance into the second medical device 110 with every angular displacement. To facilitate quick connection, it is contemplated that less than a full turn to fully mesh and engage the respective threads 135, 133 can be desirable. It is contemplated that a single-point thread mill can be used to create the threaded forms described herein.

Timed threads are thought to be particularly advantageous to the exemplary medical device connection mechanisms contemplated herein because of visibility and time constraints in the operating room. If a surgeon or technician can assemble orthopedic instrument assemblies 100 having an exemplary medical device connection mechanism 150 without looking at the assembly and know that the assembly is fully assembled and secured when the first medical device 105 is rotated a known number of degrees ("°") (e.g., 90° in certain embodiments), the surgeon can continue with the procedure with minimal interruption. This can ultimately contribute to less patient time under anesthesia and improved patient safety.

Furthermore, without being bound by theory, it is contemplated that the use of trapezoidal and timed threads in exemplary embodiments, together with the interrupted threaded portion 118 and the discontinuous threaded portion 121, can permit the respective threads 133, 135 to mesh (i.e., in the assembled configuration) faster (e.g., in a quarter turn) than a fully threaded connection. A fully threaded connection would require several turns to engage the respective components and could result in the components not fully threading into one another, which could undermine the stability of the connection, especially when subject to impaction forces common in orthopedic procedures.

It will be further appreciated that exemplary orthopedic medical device connection mechanisms 150 in accordance with this disclosure effectively transfer impaction forces around the meshed screw threads 133, 135, when the orthopedic medical device connection mechanism 150 is in the assembled configuration. This feature can reduce wear of the connection mechanism 150 during use, while permitting quick assembly and disassembly of orthopedic medical devices having the mating components of the connection mechanism 150, which can ultimately contribute to a reduction in patient time under anesthesia.

Although the protrusion 115 has been described herein as extending from the first medical device 105 and the discontinuous threaded form 121 has been described as being disposed within the hole 127 of the second medical device 110, it will be appreciated that in other exemplary embodiments, the protrusion 115 can extend from the second medical device 110 and be configured to mate (in any manner described throughout this disclosure) with a discontinuous threaded form 121 disposed within a hole 127 of the first medical device 105.

Although complementary threads 133, 135 are considered to be the most robust and reliable type of engagement mechanism for the exemplary medical device engagement mechanisms described herein, it will be appreciated that all other rotationally engaged mechanical engagement mechanisms are considered to be within the scope of this disclosure. Non-limiting examples of such other rotationally engaged mechanical engagement mechanisms can include one or more further protrusions extending from the first medical device 105, which may include (by way of further example) one or more hooks, clamps, clasps, ramps, ledges, or ridges, and one or more receivers disposed in the second medical device 110, the one or more receivers being configured to closely receive the one or more further protrusions from the first medical device 105. The further receivers may include (by way of further example) one or more complementary rods, clamps, clasps, ramps, loops, arches, ledges, recessions, gaps, or ridges configured to closely receive the one or more further protrusions from the first medical device 105. It will be appreciated that in other exemplary embodiments, the receiver(s) can be on the first medical device 105 and the further protrusions can be on the second medical device 110. Combinations and permutations of the forgoing are considered to be within the scope of this disclosure.

Referring back to FIGS. 1 and 2, the example first medical device 105 (FIG. 1B) and the second example medical device 110 (FIG. 2) are shown in a disassembled configuration. Likewise, it will be appreciated that the exemplary medical device connection mechanism 150 (FIG. 5) is shown in a disassembled configuration. To place the exemplary orthopedic instrument assembly 100 having an exemplary connection mechanism 150 into an assembled configuration, the interrupted threaded portion 118 of the protrusion 115 can be slid into the threadless channels 123 of the discontinuous threaded portion 121 of the second medical device 110. Because the threadless channels 123 are desirably keyed slots 123, it is contemplated that the interrupted threaded portion 118 can be inserted into the threadless channels 123 quickly with limited or no visibility. When the interrupted threaded portion 118 is inserted into the threadless channels 123, the orthopedic instrument assembly (and by extension, the exemplary medical device connection mechanism 150 itself) 100 can be said to be in a "preassembled" configuration (see FIGS. 8A and 9). Rotating the protrusion 115 and the interrupted threaded portion 118 to engage the threads of the discontinuous threaded portion 121 places the exemplary orthopedic instrument assembly 100 into an "assembled" configuration (see FIGS. 7 and 8B).

In the exemplary assemblies depicted in FIGS. 1-8B, the protrusion 115 is fixedly engaged to a base 116, such that the entire first medical device 105 (which is an adaptor in the depicted exemplary embodiments) rotates with the protrusion 115 to place the exemplary orthopedic instrument assembly 100 in the assembled configuration. However, in other exemplary embodiments, it is contemplated that the protrusion 115 can rotate independently of the base 116.

In embodiments, it is contemplated that markings or other indicia may be provided to indicate the starting position of the preassembled configuration and the engaged position of the fully assembled configuration.

Figure 9:
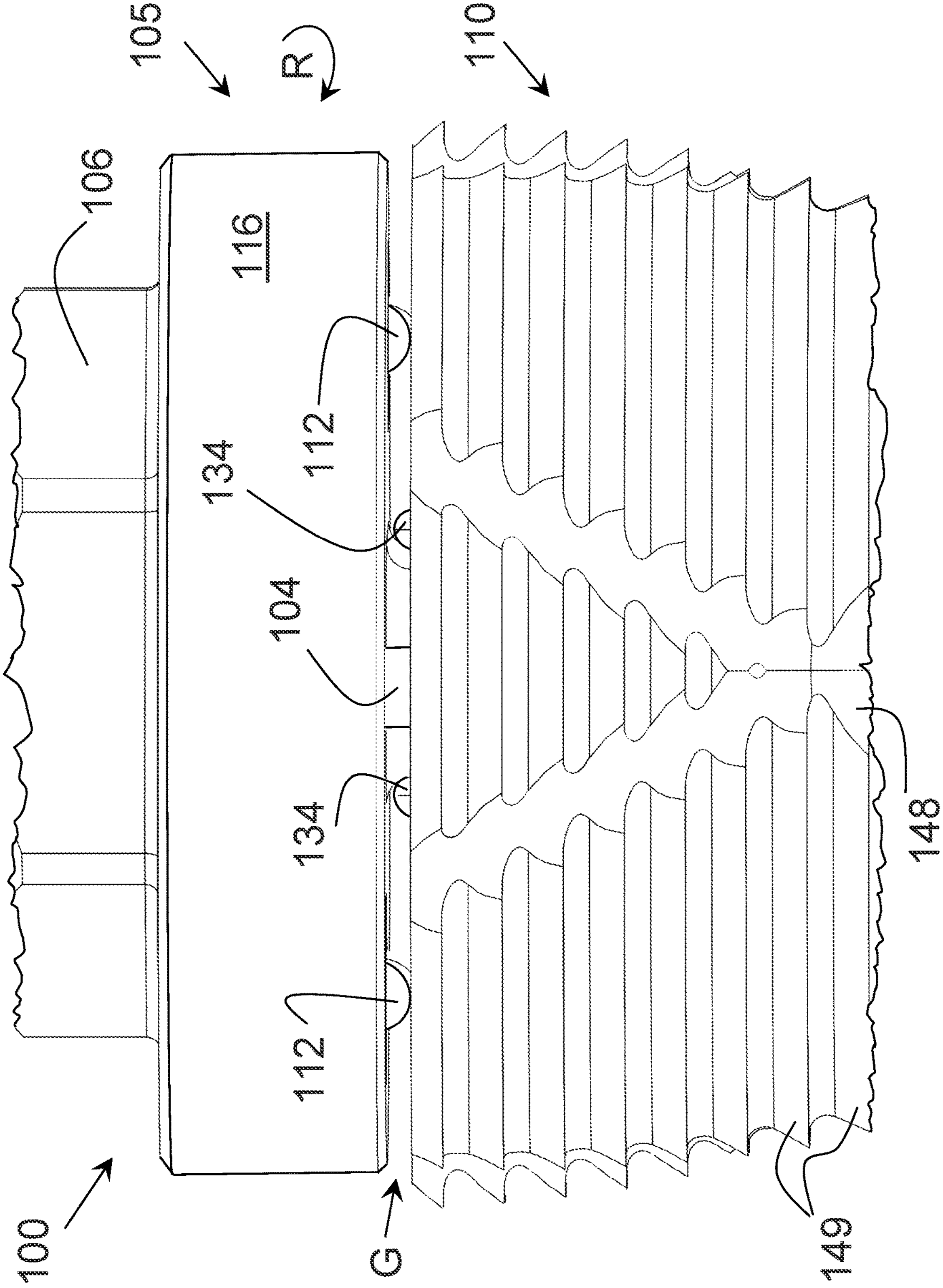
FIG. 9 is a facing view of an exemplary orthopedic instrument assembly in a pre-engagement configuration.

Referring to FIG. 9, which depicts an exemplary orthopedic instrument assembly 100 in a preassembled configuration, a moveable non-rigid spacer 112 is desirably disposed within the gap G created between a distal side 103 of the base 116 of the first medical device 105 and the proximal side 124 of the second medical device 110. In the depicted embodiment, the moveable non-rigid spacer 112 retracts into the base 116 of the first medical device 105 as the orientation of the orthopedic instrument assembly 100 is changed from the preassembled configuration (FIG. 9) to the assembled configuration (see FIG. 7) via rotation R. It will be appreciated that in other exemplary embodiments, the moveable non-rigid spacer 112 can retract into the second medical device 110 as the orientation of the orthopedic instrument assembly 100 is changed from the preassembled configuration to the fully assembled configuration. All types of spacers that can be compressed, deformed, or retracted are considered to be within the scope of this disclosure. Non-limiting examples of moveable non-rigid spacers 112 include a ball plunger, a retractable pin, or an o-ring.

In the embodiments depicted in FIGS. 1-3, two moveable non-rigid spacers 112 are desirably provided at equal and opposite positions within the base 116 to reduce friction evenly as the orientation of the exemplary orthopedic instrument assembly 100 is rotated from the preassembled configuration to the assembled configuration. However, it will be appreciated that in other exemplary embodiments, a single moveable non-rigid spacer 112 may be provided. In yet other exemplary embodiments, more than two moveable non-rigid spacers 112 may be provided. In exemplary embodiments involving two or more moveable non-rigid spacers 112, it will be appreciated that the two or more moveable non-rigid spacers 112 can be evenly spaced relative to one another, or unevenly spaced.

In the depicted embodiments, a moveable non-ridged spacer receiver 134 is disposed in the proximal surface 122 of the proximal side 124 of second medical device 110. The moveable non-rigid spacer 112 of the first medical device 105 is disposed within the moveable non-ridged spacer receiver 134 when the orthopedic instrument assembly 100 is in the assembled configuration. It will be appreciated that the moveable non-rigid spacer 112 and the moveable non-ridged spacer receiver 134 (if present) can be disposed on either the first medical device 105, the second medical device 100, or both the first medical device 105 and the second medical device 110 in exemplary embodiments.

The depicted first medical device 105 further comprises a pin 104 extending from the distal side 103 of the base 116. The pin 104 can be used to align the first medical device 105 relative to the second medical device 110 in the preassembled configuration. The user aligns the pin 104 over a first end 166 of an arcuate groove 136 disposed in the proximal side 124 of the second medical device 110 while inserting the protrusion 115 of the first medical device 105 into the threadless channel 123 of the discontinuous threaded portion 121 of the second medical device 110. The combination of pin 104 and the arcuate groove 136 can provide both quick visual and haptic feedback that the exemplary orthopedic instrument assembly 100 is in the preassembled configuration and is properly aligned to be fully assembled. Stated differently, the pin 104 and the arcuate groove 136 can be desirable user indicators to communicate proper alignment of the timed screw threads 133, 135 of the connection mechanism 150.

As the user rotates the preassembled orthopedic instrument assembly 100 to place the orthopedic instrument assembly 100 into the assembled configuration, the pin 104 rotates with the base 116 and extends deeper into the opposingly oriented arcuate groove 126 until the pin 104 reaches the accurately distant second end 167 of the arcuate groove 136. It will be appreciated that the pin 104 and groove 136 (if collectively present) can be disposed on either the first medical device 105, the second medical device 100, or both the first medical device 105 and the second medical device 110 in embodiments. It will further be appreciated that the screw threads 133, 135 can be arranged for clockwise or counterclockwise rotation.

In exemplary embodiments comprising timed threads 133, 135, the gap G is effectively eliminated as the users rotates the orthopedic instrument assembly 100 from the preassembled configuration into the assembled configuration, thereby providing further haptic feedback to the user that the first medical device 105 has engaged the second medical device 110.

Referring collectively to the particular embodiments of FIGS. 1-11, these particular examples depict an orthopedic instrument assemblies 100 configured for use in a knee arthroplasty.

Briefly, in a typical knee arthroplasty procedure, the surgeon makes a generally vertical medial parapatellar incision of about five to six inches in length on the anterior or anteromedial aspect of the knee.

The surgeon then continues to incise the fatty tissue to expose the anterior or anteromedial aspect of the joint capsule. The surgeon may then perform a medial parapatellar arthrotomy to pierce the joint capsule. A retractor may then be used to move the patella generally laterally (roughly about 90 degrees) to expose the distal condyles of the femur and the cartilaginous meniscus resting on the proximal tibial plateau. The surgeon then removes the meniscus and uses instrumentation to measure and resect the distal femur and proximal tibia to accommodate trial—and then eventually final—implants.

To prepare the resected tibia 180 (FIG. 12) for the tibial component of an endoprosthetic knee implant, surgeons can insert a series of progressively larger broaches into the proximal tibial metaphysis and diaphysis to create a pocket in the bone that mirrors the shape and size of the selected implant or implants. Broaching instrumentation often includes a broach (sec FIGS. 2 and 3) with a mating attachment geometry and an adapter (see FIG. 1) that attaches to an impaction handle (see FIGS. 4 and 5).

The proximal tibia 180 can present voids and sections of poor bone quality that compromise the overall stability of a tibial implant construct. Surgeons can use conical implants (sec FIGS. 11 and 12) to fill and reinforce these sections to help prevent further bone degradation and to improve structural integrity of the bone surrounding the tibial implants.

Referring back to FIG. 1, in the depicted example, the first medical device 105 is an adaptor that is configured to mate with the broach of FIG. 2 (i.e., an example second medical device 110). The protrusion 115 is a shaft that extends from the base 116 of the adaptor, preferably from the distal side 103 of the base 116. In preferred embodiments, a pin 104 and a ball plunger (i.e., an example moveable non-rigid spacer 112) also extend from the distal side 103 of the base 116. Either the pin 104, or the moveable non-rigid spacer 112, or both the pin 104 and the moveable non-rigid spacer 112 can be used to help align the timed screw threads 133, 135 and assemble the first medical device 105 and the second medical device 110 in the manner described above.

In the depicted exemplary embodiment, the first medical device 105 (i.e., the adaptor) further comprises a receiver construct 101 extending from a proximal side 108 of the base 116. The receiver construct 101 comprises a receiver construct base 106 extending from the proximal side 108 of the base 116, a bridge 102 extending proximally from the receiver construct base 106, and a receiver backstop 107 extending proximally from the bridge 102. The bridge 102 desirably has a cross-sectional area that is less than the cross sectional area of the receiver construct base 106 and the receiver backstop 107 when bisected along a transverse plane. In the depicted embodiment, the receiver construct 101 is generally cylindrical, and the bridge 102 and adjacent walls of the receiver construct base 106 and the receiver backstop 107 define an annular gap 131 that can be filled by an engagement protrusion (e.g., an annular follower 156) of a positioning instrument (FIGS. 4 and 5) to thereby selectively engage the first medical device 105.

Referring back to FIGS. 2 and 3, in the depicted example, the second medical device 110 is a broach that is configured to mate with the adapter of FIG. 1. The example second medical device 110 comprises an interior sidewall 129. The interior sidewall 129 defines a hole 127 extending into the body 126 of the second medical device 110. A discontinuous threaded portion 121 is disposed within the hole 127. Threads 133 of the discontinuous threaded portion 121 extend from the interior sidewall 129 radially inward toward a center longitudinal axis C (FIG. 8A) of the hole 127. The discontinuous threaded portion 121 defines a threadless channel 123 extending along a discontinuous threaded portion height tpH. The discontinuous threaded portion 121 can receive the interrupted threaded portion 118 of the protrusion 115 of the first medical device 105 through the threadless channel 123. The outer side 146 of the depicted second medical device 110 further comprises multiple broach teeth 149 arranged generally circumferentially along the height of the second medical device 110. The outer side 146 and the multiple broach teeth 149 can define one or more chip breaches 148. When one of the medical devices in accordance with this disclosure is a broach, chip breaches 148 disposed on the outer side of the broach permit marrow and other metaphyscal and/or diaphyseal tissue to be broken up as "chips" and evacuated from the chip breaches 148 to facilitate broaching. The chip breaches 148 are desirably disposed at an angle on the outer side 146 such that an end of a chip breach 148 located closer to the distal side 147 of the second medial device 110 is offset from an end of the chip breach 148 located closer to the proximal side 124 of the second medical device 110. Without angled chip breaches 148, tissue is more likely to be evacuated as longer ribbons, or evacuation could be hindered altogether.

It will be appreciated that the first medical device 105 and the second medical device 110 can be manufactured from materials that have desirable physical and chemical properties for the intended purpose. For example, when the first medical device 105 and the second medical device 110 are reusable orthopedic instruments, the material may be stainless steel or other suitable clinically tested material. In examples where the first medical device 105, second medical device 110, or components thereof are designed to be disposable or for limited use, the materials can be selected from the group consisting essentially of polyether ether ketone ("PEEK"), polyethylene (including but not limited to ultra-high molecular weight polyethylene ("UHMWPE") and cross-linked polyethylene ("XLPE")) ("PE"), and polyamide (including but not limited to a glass-filled polyamide and a carbon fiber filled polyamide).

In exemplary embodiments wherein scratching between the first medical device 105 and the second medical device 110, or components thereof is desired to be minimized, the first medical device 105, the second medical device 110, or engaging components thereof can be manufactured from PEEK. In one exemplary embodiment, the protrusion 118 can be made of PEEK while the remainder of the first medical device 110 is not made from PEEK. In other exemplary embodiments, the first medical device 105, second medical device 110, or components thereof can be coated to further reduce visible signs of wear, to further reduce the coefficient of friction, or to accommodate patient allergies. A non-limiting example list of coatings includes cobalt chromium molybdenum alloys, zirconium oxides, and niobium nitrides. In other exemplary embodiments, the threads 135 of the interrupted threaded portion 118 can indirectly engage the threads 133 of the discontinuous threaded portion 121 in the assembled configuration. In such exemplary embodiments, a liner or other intermediate structure can be disposed between the respective threads 133, 135 in the assembled configuration. Such liners can be made from materials selected for the desired purpose. Such materials may include any of the materials listed herein.

FIGS. 4 and 5 depict an exemplary orthopedic instrument assembly 100 in an assembled configuration that is selectively fixedly engaged to a positioner 153 (e.g., a handle). As better seen in FIG. 5, which is a detailed perspective cross-sectional side view of the embodiment depicted in FIG. 4, the positioner 153 engages the bridge 102 of the receiver construct 101 via a biasing engagement mechanism 155. All biasing engagement mechanisms 155 known to persons having ordinary skill in the art are considered to be within the scope of this disclosure. In the depicted embodiment, the biasing engagement mechanism 155 comprises a biasing spring 157 disposed within a housing 159 of the positioner 153. The biasing spring 157 exerts a biasing force to an annular follower 156 that encircles the bridge 102 of the receiver construct 101 of the first medical device 105 when the receiver construct 101 is disposed within the positioner 153. The annular follower 156 in turn applies the biasing force to the bridge 102, which distributes these forces through the receiver backstop 107 and the receiver construct base 106 and into the adjacent housing 159 of the positioner 153 to thereby fixedly engage the first medical device 105 of the exemplary orthopedic instrument assembly 100.

To disengage the first medical device 105 from the positioner 153, a user can depress the exposed button 154 of the biasing engagement mechanism 155, which overcomes the biasing force of the biasing spring 157, thereby releasing the bridge 102 from the annular follower 156 and permitting the user to remove the first medical device 105 from the positioner 153. In this manner, the exemplary orthopedic instrument assembly 100 can be said to be "selectively fixedly engaged" to a positioner 153.

FIG. 5 further depicts an exemplary medical device connection mechanism 150 in the assembled configuration. The threads 135 of the interrupted threaded portion 118 had been inserted through the threadless channel 123 of the of the discontinuous threaded portion 121 of the second medical device 110 (e.g., a broach) and had been rotated to be disposed between and closely received by adjacent threads 133 of the discontinuous threaded portion 121 to thereby engage the threads 133 of the discontinuous threaded portion 121. To disengage the medical device connection mechanism 150 and thereby place the orthopedic instrument assembly in a disassembled configuration, the user can rotate the second medical device 110 relative to the first medical device 105 such that the threads 135 of interrupted threaded portion 118 disengage the threads 133 of the discontinuous threaded portion 121 and move towards the threadless channel 123 relative to the second medical device 110. Once the threads 135 of the interrupted threaded portion 118 are in the threadless channel 123, the first medical device 105 can be withdrawn longitudinally from the second medical device 110 to thereby place the exemplary orthopedic instrument assembly in a disengaged configuration.

Figure 6:
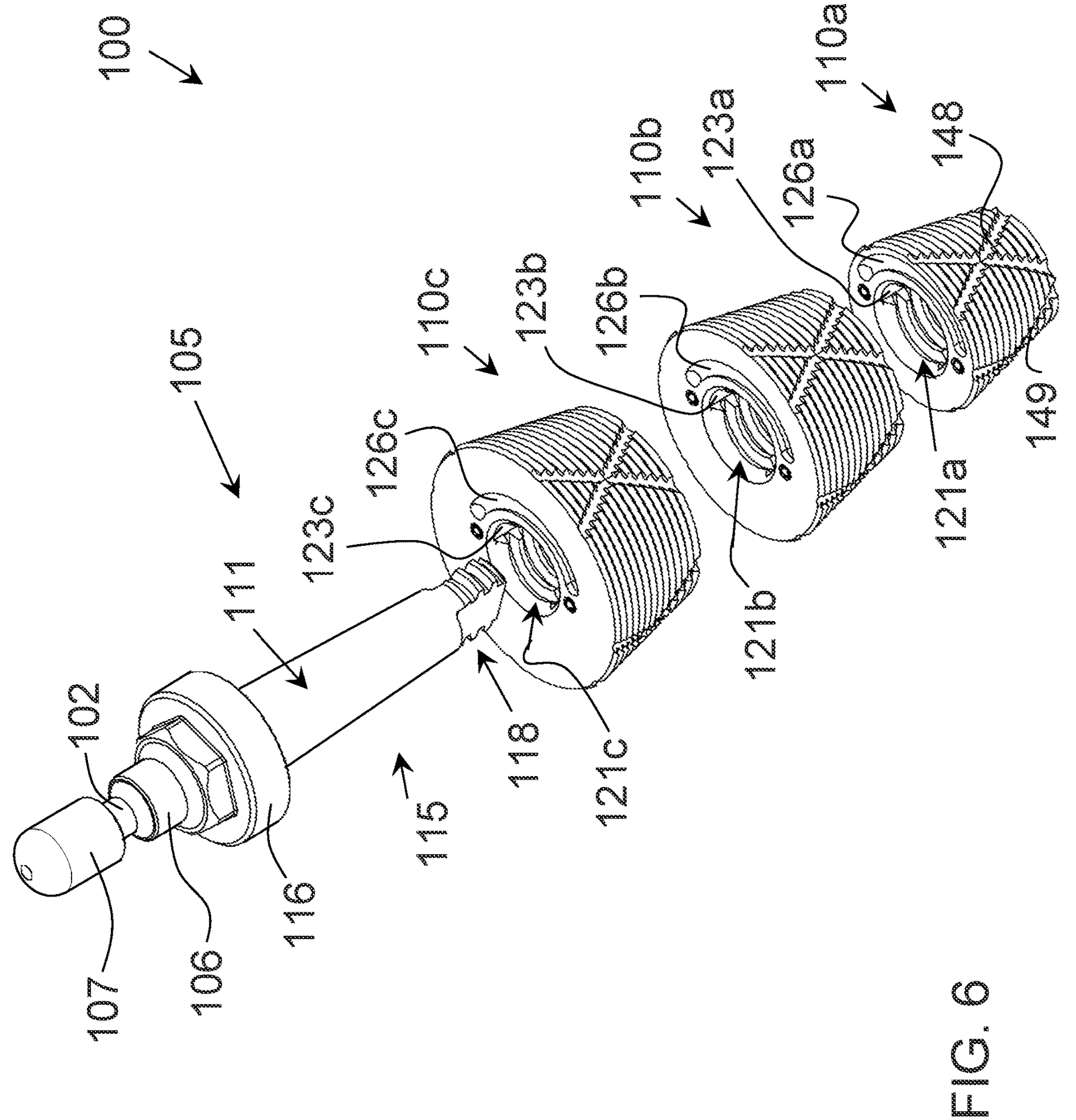
FIG. 6 is an isometric expanded view of an exemplary orthopedic instrument assembly having an exemplary medical device connection mechanism; the exemplary orthopedic instrument assembly comprises stacked modular orthopedic instruments, depicted in a disassembled configuration.
Figure 7:
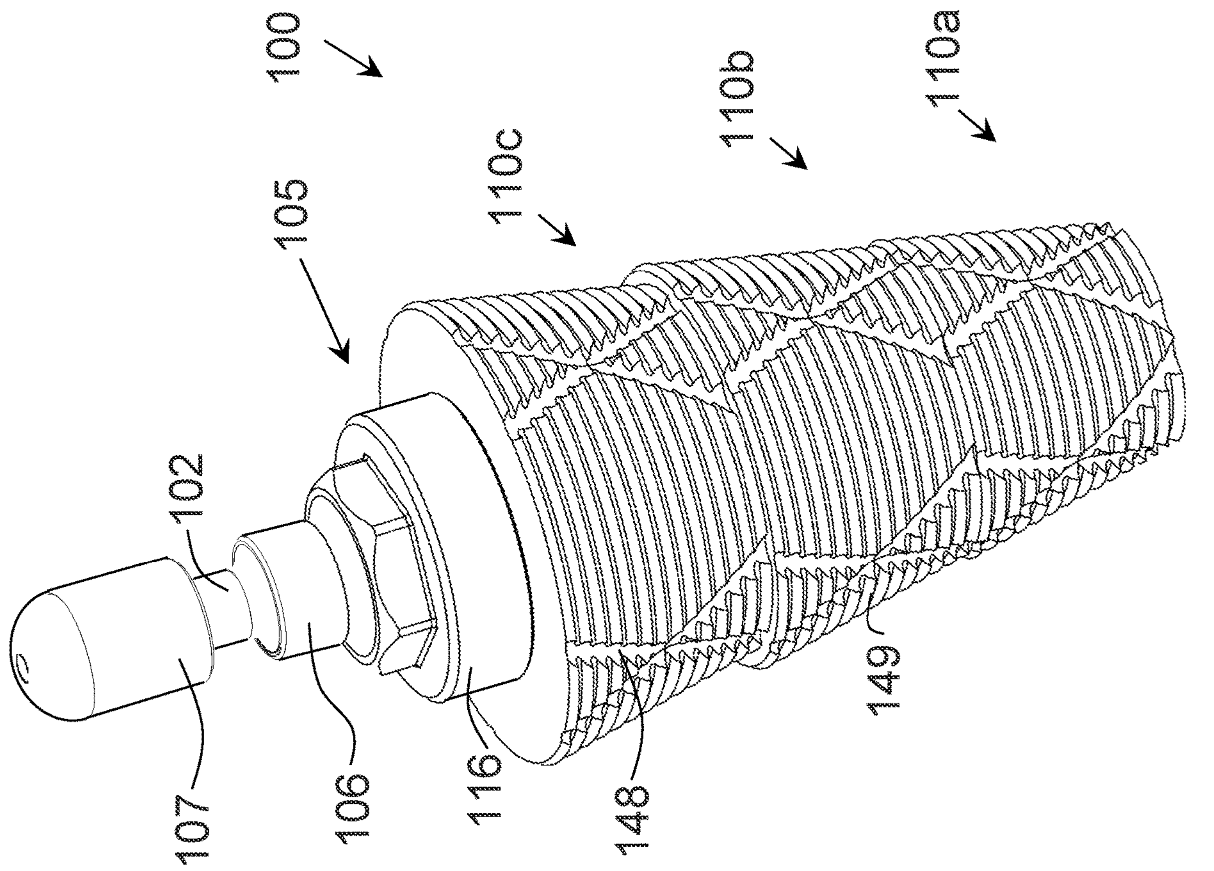
FIG. 7 is an isometric view of the exemplary orthopedic instrument assembly of FIG. 6, depicted in an assembled configuration.

FIGS. 6 and 7 are perspective views of another exemplary orthopedic instrument assembly 100 comprising an exemplary medical device connection mechanisms 150, wherein multiple additional medical devices 110*b*, 110*c* are disposed between the first medical device 105 and the second medical device 110*a* when the medical device connection mechanism 150 is placed in an assembled configuration. In the depicted embodiment, each additional medical device 110*b*, 110*c* disposed between the first medical device 105 and the second medical device 110*a* comprise two opposing threadless channels 123*b*, 123*c* and each is capable of engaging an interrupted threaded portion 118 of a protrusion 115 of a first medical device 105 as described above. The first medical device 105 of the depicted embodiment has a longer protrusion 115 than the protrusion 115 depicted in FIG. 1. In practice, the distal end 119 of the protrusion 115 depicted in FIGS. 6 and 7 can extend through the opposing threadless channels 123*c*, 123*b*, of the additional medical devices 110*b*, 110*c* and into the opposing threadless channels 123*a* of the second medical device 110 to place the exemplary orthopedic instrument assembly 100 in a preassembled configuration. When the interrupted threaded portion 118 is rotated out of the opposing threadless channels 123*a* of the second medical device 110 to mesh with the adjacent threads 133 of the discontinuous threaded portion 121 of the second medical device 110, the exemplary orthopedic instrument assembly 100 (and by extension, the exemplary medical device connection mechanism 150) can be said to be in the "assembled configuration." In FIGS. 6-7, the second medical device 110*a* and each additional medical device 110*b*, 110*c* (e.g., the third medical device 110*b*, and fourth medical device 110*c*) are stackable broaches. However, it will be appreciated that other types of medical devices can be used in other embodiments.

In the depicted embodiment, the fourth medical device 110*c* is sized to be smaller than the third medical device 110*b* to accommodate the natural tapering of the bone into which the assembled orthopedic instrument 100 will in inserted. In exemplary embodiments, the third medical device 110*b* can be the same size as the second medical device 100*a*. In other exemplary embodiments, the sizes of any of the provided medical devices can differ from the sizes of one or more sizes of the other provided additional medical devices. It is contemplated that additional medical devices 110*b*, 110*c* having exemplary medical device connection mechanisms 150 in accordance with this disclosure, permit true modularity (i.e., the interchangeable use of any of the second, third, fourth, or further medical devices 110*a*, 110*b*, 110*c* . . . with the first medical device 105 (e.g., an adaptor)). Without being bound by theory, it is contemplated that exemplary orthopedic instrument assemblies 100 having true modularity as contemplated by this disclosure may permit users to assemble a desired broach assembly quickly to better broach a desired portion of a desired bone in a way that accommodates the patient's unique natural anatomy while minimizing inventory.

It will be appreciated that in other exemplary embodiments, the protrusion 115 can comprise multiple interrupted threaded portions, wherein an interrupted threaded portion of the multiple interrupted threaded portions can further engage a discontinuous threaded portion 121*b*, 121*c* of an additional medical device 110*b*, 110*c* disposed between the first medical device 105 and the second medical device 110 in an assembled configuration. The threads 135, 133 of the respective threaded portions are desirably timed as described above. It will be appreciated that in embodiments comprising multiple additional medical devices 110*b*, 110*c*, the protrusion 115 may be displaced less angularly (when moving from the preassembled configuration to the assembled configuration) compared embodiments in which no additional medical devices 110*b*, 110*c* are present.

Figure 8A:
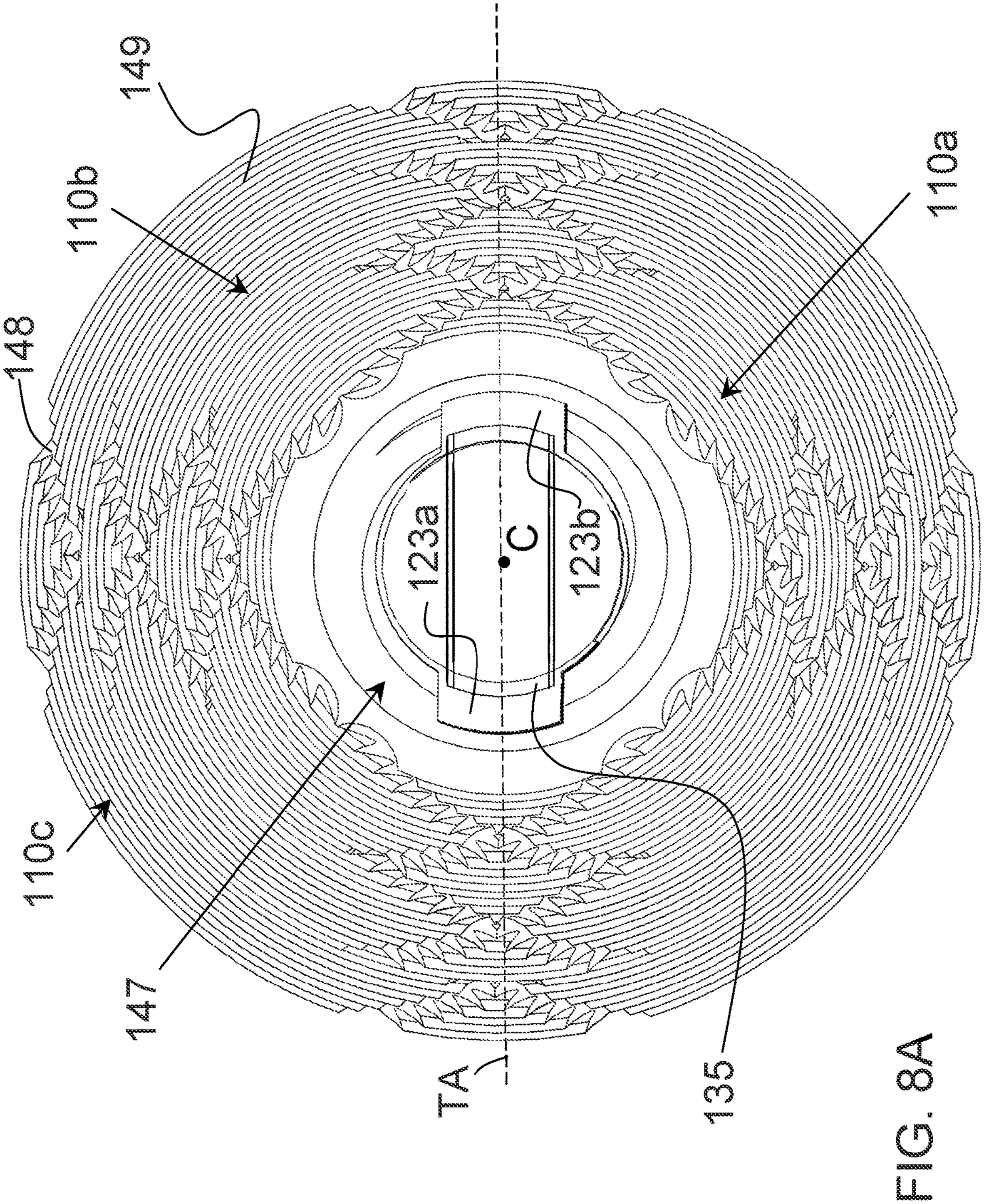
FIG. 8A is a bottom view of the exemplary orthopedic instrument assembly of FIG. 7, depicted in a partially assembled configuration.
Figure 8B:
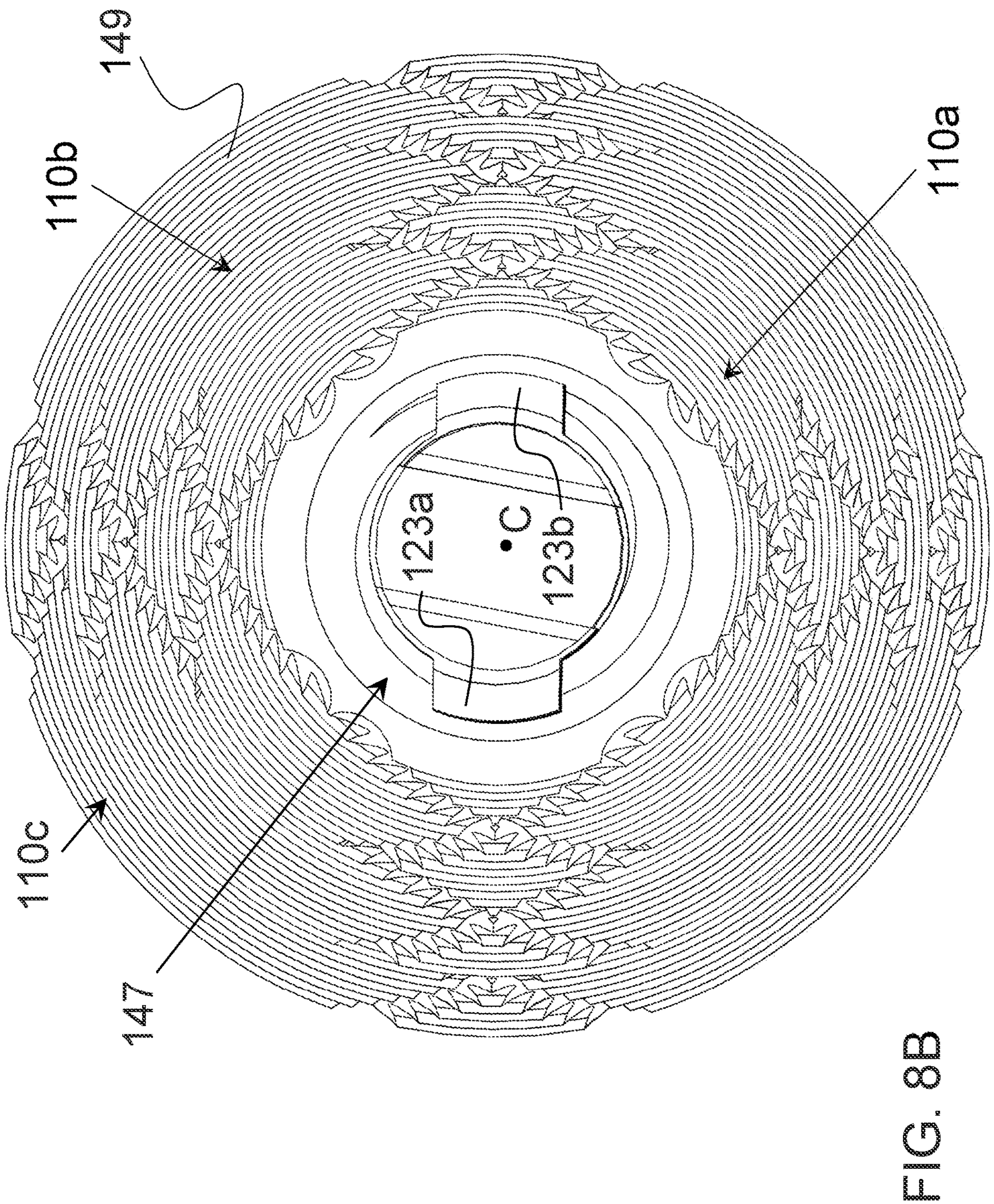
FIG. 8B is a bottom view of the exemplary orthopedic instrument assembly of FIG. 7, depicted in a fully assembled configuration.

FIG. 8A is a bottom view of the exemplary orthopedic instrument assembly 100 of FIGS. 6 and 7 shown in a preassembled configuration. FIG. 8B is a bottom view of the exemplary orthopedic instrument assembly 100 of FIGS. 6 and 7 shown in an assembled configuration.

Although the figures generally depict the hole 127 extending into the center of the body 126 of a second medical device 110 that is generally symmetrical around a bisecting coronal and sagittal plane, nothing in this disclosure limits the invention to the depicted embodiments. In other exemplary embodiments, the hole 127 and therefore the discontinuous threaded portion 121 can be disposed closer to a portion of a distal side 147 of the body 126 of the second medical device 110 than another portion of the distal side 147. Furthermore, in other exemplary embodiments the first or second medical device 105, 110 can be asymmetric, symmetric around a single bisecting plane, symmetric around multiple bisecting planes, or radially symmetric.

In the embodiments depicted and described with reference to FIGS. 2-8B, the second medical device 110 is a bone preparation instrument. Common bone preparation instruments include broaches (see FIGS. 2-8B), rasps, reamers, keel punches, and other cutting instruments. However, it will be appreciated that in other exemplary embodiments, the second medical device 110 can be an orthopedic instrument other than a bone preparation instrument. Such instruments can include measurement instruments, visualization instruments, and combinations thereof. Combinations and permutations of measurement instruments or visualization instruments with bone preparation instruments are considered to be within the scope of this disclosure.

The example embodiments depicted and described with reference to FIGS. 2-8B, can be particularly adapted to prepare a proximal tibia 180 for one or more conical tibial inserts 160 (see FIGS. 11 and 12). Conical tibial inserts 160 are a type of orthopedic endoprosthetic implant. Conical tibial inserts 160 are typically used when an operative tibia 180 presents with voids or sections of poor bone quality. The surgeon can ream, broach, or otherwise remove trabecular bone from the metaphysis and/or diaphysis to create a pocket that generally complements and mirrors the outer dimensions of the conical tibial insert 160. Once inserted, the conical tibial insert 160 reinforces the metaphyseal and/or diaphyseal sections of the tibia 180 to further reduce bone degradation and to improve the structural integrity of the bone surrounding the tibial components of an endoprosthetic knee implant.

The modular orthopedic instrument assembly 100 of FIGS. 6 and 7 is an example broaching instrument having an exemplary mechanical connection mechanism 150. The depicted broaching instrument is desirably also provided with complementary tibial conical inserts 160 that have outer dimensions that mirror or otherwise complement the outer dimensions of the broach construct (i.e., any additional medical devices 110*b*, 110*c* disposed between the first medical device 105 and the second medical device 110). The tibial conical inserts 160 can desirably be modular tibial conical inserts. In this manner, the surgeon can select sizes and shape of additional medical devices 110*b*, 110*c* (e.g., modular tibial broaches having a component of an exemplary connection mechanism 150 in accordance with this disclosure) that are appropriate for the particular anatomy of the operative patient's tibia 180. The surgeon can then assemble the exemplary orthopedic instrument assembly 100 in the manner described above. Once assembled, the surgeon can position the broaching instrument over the resected tibia 180 and use a hammer or other impaction tool to broach the proximal tibia 180 to create a pocket that complements the outer dimensions of the provided tibial conical insert(s) 160 (FIG. 12).

Figure 10:
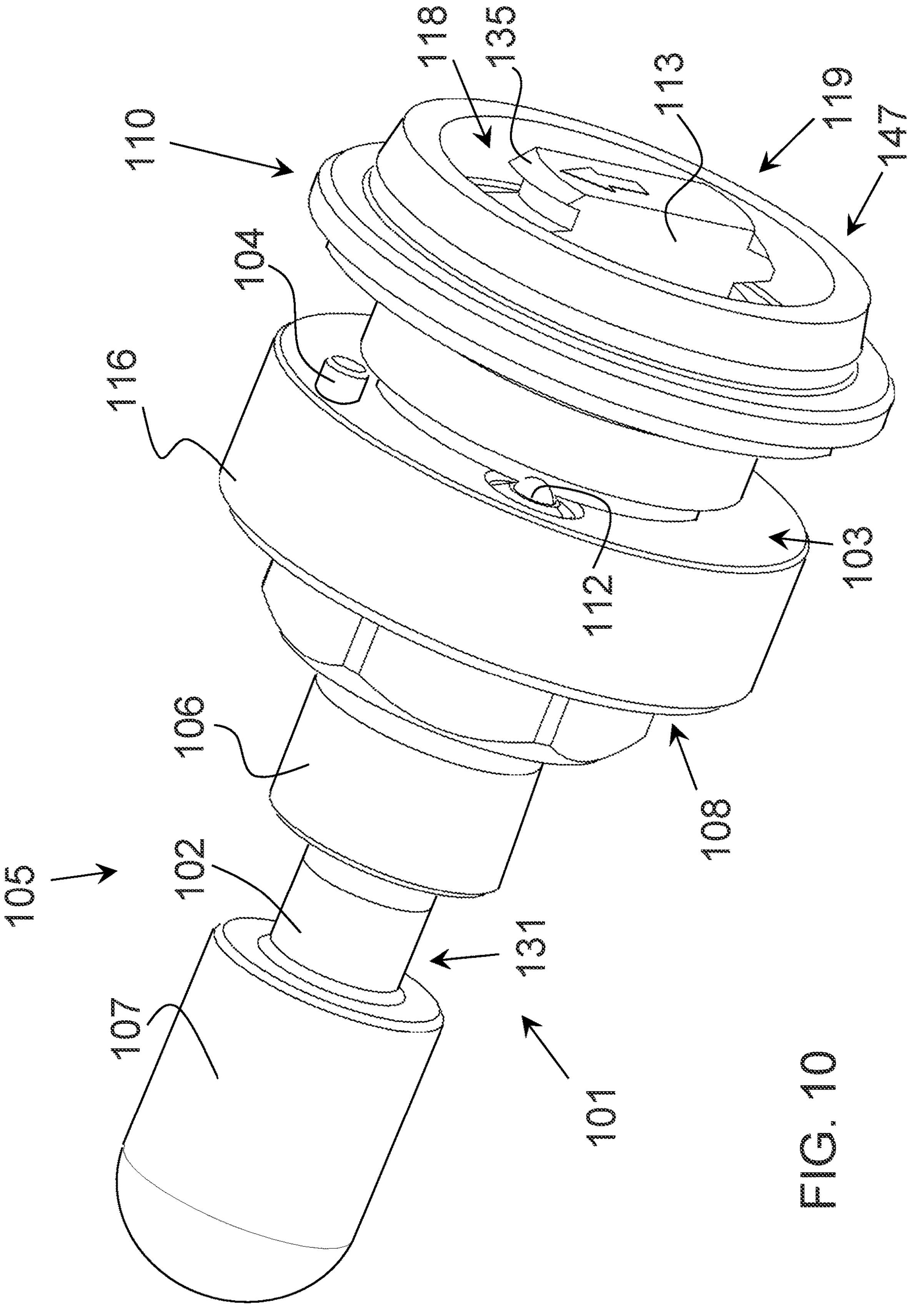
FIG. 10 is an isometric view of an exemplary orthopedic instrument assembly in an assembled configuration, wherein the second medical device of the depicted orthopedic instrument assembly is a secondary adaptor.

Because the provided tibial conical insert(s) 160 are complementary to the outer dimensions of the broaches, the created pocket in the tibia 180 can closely receive the tibial conical insert(s) 160. FIGS. 10-12 illustrate this concept.

Figure 11:
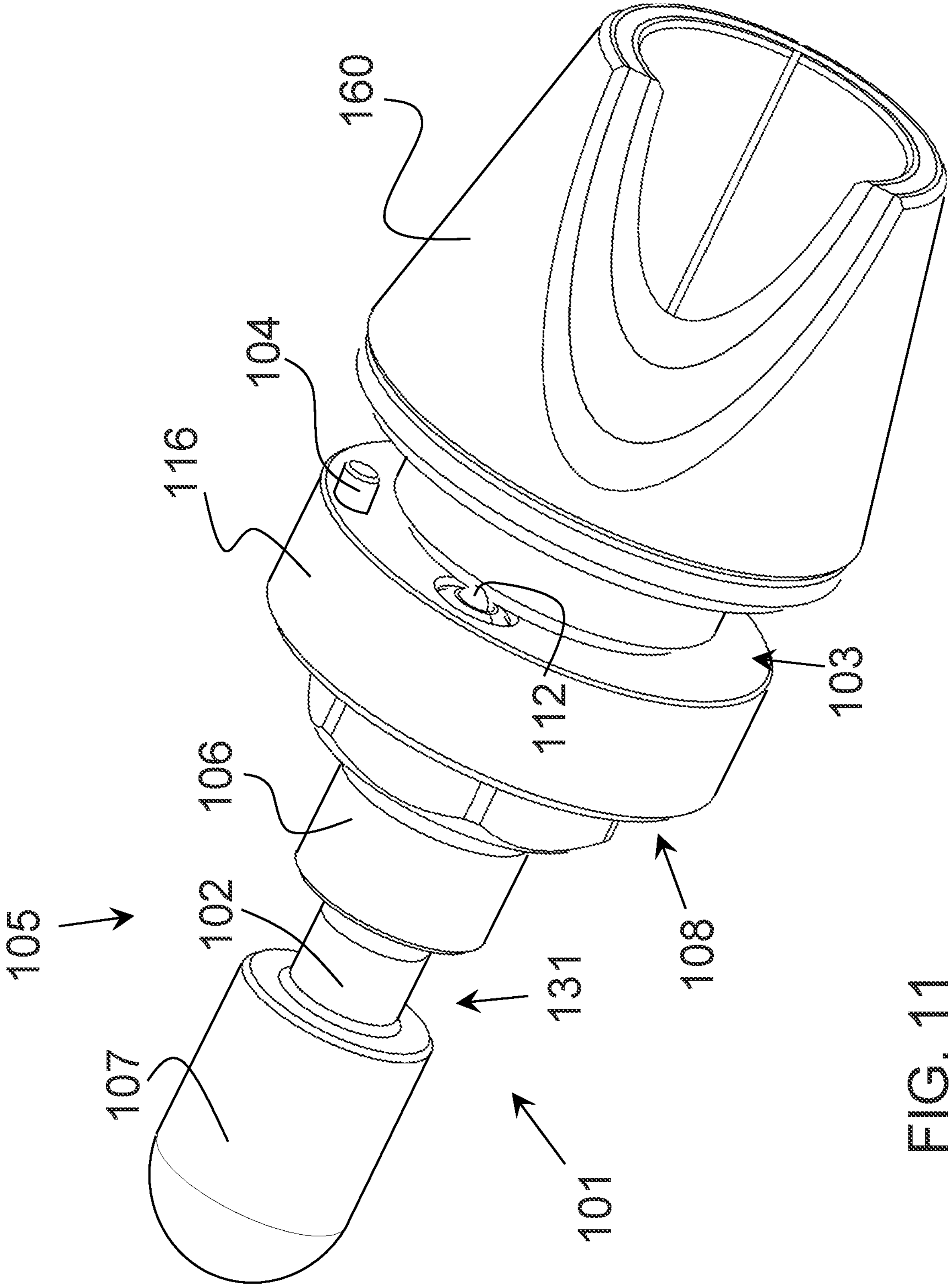
FIG. 11 is an isometric view of the orthopedic instrument assembly of FIG. 10 further depicting an endoprosthetic implant engaged to the secondary adaptor.
Figure 12:
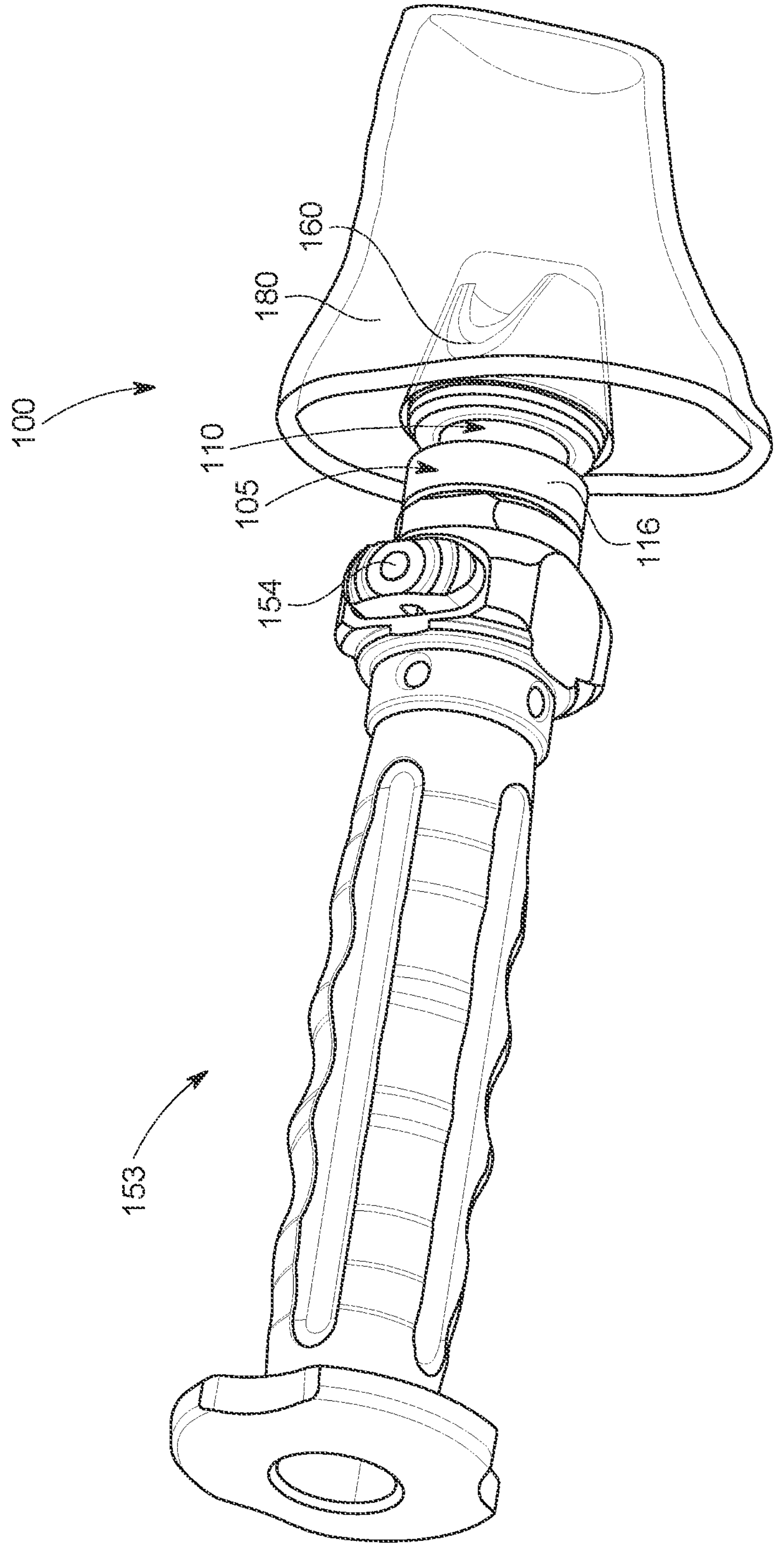
FIG. 12 is an isometric view of the orthopedic instrument assembly of FIG. 11 engaged to a positioner, wherein the endoprosthetic implant has been inserted into a resected proximal tibia.

FIG. 10 depicts an exemplary orthopedic instrument assembly 100 in an assembled configuration in which the first medical device 105 is an adaptor and the second medical device 110 is a secondary adaptor configured to selectively engage a conical tibial insert 160 (FIG. 11). FIG. 11 shows the conical tibial insert 160 selectively engaged to the orthopedic instrument assembly 100 via a wedge taper. FIG. 12 illustrates the exemplary orthopedic instrument assembly 100 of FIG. 11 further being attached to a positioning member 153 (e.g., a handle), wherein the conical tibial insert 160 is being placed into the pocket in the resected proximal tibia 180 that was created by a broaching orthopedic instrument assembly 100 such as the ones depicted in any of FIGS. 1-8B.

In other exemplary embodiments, the second medical device 110 can be an orthopedic implant configured to receive the protrusion 115 of the first medical device 105 (sec FIG. 11). A non-limiting list of example orthopedic implants include, but is not necessarily limited to: tibial cones, femoral cones, tibial and femoral components of endoprosthetic implants, and trial implants of any of the foregoing.

In other exemplary embodiments, the second medical device 110 can be a secondary adaptor (FIG. 10). In such exemplary embodiments, the secondary adaptor can be further configured to selectively engage an orthopedic instrument, or an orthopedic implant, or a further adaptor (see FIG. 11). In such exemplary embodiments involving a secondary adaptor, the orthopedic implant, the orthopedic instrument, or further adaptor can be said to be configured to indirectly engage the first medical device 105.

Other common orthopedic implants include implants or components thereof that extend into the metaphyseal or diaphyseal bone when implanted, other arguments, spacing elements, and void fillers. It will be appreciated that nothing in this disclosure limits the scope of this disclosure to the knee joint. All orthopedic instruments, orthopedic implants, and secondary adaptors having an exemplary connection mechanism 150 are considered to be within the scope of this disclosure.

Components of an exemplary orthopedic instrument assembly 100 can be provided in the form of a surgical kit. The components of the kit are preferably arranged in a convenient format, such as in a surgical tray or case. However, the kit components do not have to be packaged or delivered together, provided that they are assembled or collected together in the operating room for use at the time of surgery.

An exemplary kit can include any suitable embodiment of an exemplary orthopedic instrument assembly 100, variations of the exemplary orthopedic instrument assemblies 100 described herein, and any other exemplary orthopedic instrument assembly according to an embodiment. While it is contemplated that an exemplary kit may include one or more first medical devices 105 (preferably of difference sizes), one or more second medical devices (preferably of different sizes) and one or more additional medical devices 110*b*, 110*c* (preferably of different sizes) configured to be disposed between the first medical device 105 and the second medical device 110 in the assembled configuration, it will be appreciated that certain kits may lack some or all of these elements.

Any suitable embodiment of a first medical device 105, variations of the first medical devices 105 described herein, and any other first medical device 105 according to an embodiment, are considered to be within the scope of this disclosure. Any suitable embodiment of a second medical device 110, variations of second medical devices 110 described herein, and any other second medical device 110 according to an embodiment are considered to be within the scope of this disclosure. Any suitable embodiment of an additional medical device 110*b*, variations of the additional medical devices 110*b* described herein, and any other additional medical devices 110*b* according to an embodiment, are considered to be within the scope of this disclosure.

Selection of a suitable number or type of first medical device 105, second medical device 110, and additional medical devices 110*b* (110*c*, etc.) to include in a kit according to a particular embodiment can be based on various considerations, such as the procedure intended to be performed using the components included in the kit.

An exemplary orthopedic instrument assembly can comprise: an adaptor, the adaptor comprising a shaft having a proximal end and a distal end distally disposed from the proximal end along a height of a body of the shaft, the body of the shaft comprising a shank portion disposed closer to the proximal end than the distal end, and an interrupted threaded portion disposed closer to the distal end than the proximal end; and an orthopedic instrument, the orthopedic instrument having a body, an interior sidewall, the interior sidewall defining a hole extending into the body of the orthopedic instrument, the hole configured to receive the shaft of the adaptor via a discontinuous threaded portion, the discontinuous threaded portion defining a threadless channel extending longitudinally therethrough.

Certain exemplary assemblies can further comprise an engaged configuration, wherein shaft threads of the interrupted threaded portion of the distal end of the shaft adjacently engage threads of the discontinuous threaded form of the orthopedic instrument.

In certain exemplary assemblies, the shaft threads and the discontinuous threaded threads are trapezoidal.

An exemplary orthopedic instrument assembly can comprise: an adaptor, the adaptor comprising a shaft having a proximal end and a distal end distally disposed from the proximal end along a height of a shaft body, the shaft body comprising an interrupted threaded portion disposed closer to the distal end than the proximal end; and an orthopedic instrument, the orthopedic instrument having: a body, an interior sidewall, the interior sidewall defining a hole extending into the body, a discontinuous threaded portion comprising a series of screw threads extending radially inward from the interior sidewall toward a center longitudinal axis, wherein the discontinuous threaded portion defines a threadless channel extending along a height of the discontinuous threaded portion, a threadless channel interior sidewall having: a first threadless channel edge disposed radially outward from and circularly adjacent to a first edge of the interior sidewall to define a first step disposed radially between the first edge of the interior sidewall and the first threadless channel edge, and a second threadless channel edge disposed radially outward from and circularly adjacent to a second edge of the interior sidewall to define a second step disposed radially between the second edge of the interior sidewall and the second threadless channel edge, wherein the screw threads terminate at or before the first step and the second step, wherein the first step, the second step, and the threadless channel interior sidewall define a keyed slot extending longitudinally along the orthopedic instrument, and wherein the keyed slot is configured to closely receive the interrupted threaded portion of the adaptor.

An exemplary orthopedic instrument assembly can comprise: an adaptor, the adaptor comprising a shaft having a proximal end and a distal end distally disposed from the proximal end along a height of a shaft body, the shaft body comprising an interrupted threaded portion disposed closer to the distal end than the proximal end; and an orthopedic instrument, the orthopedic instrument having: a body, an interior sidewall, the interior sidewall defining a hole extending into the body, a discontinuous threaded portion comprising a series of screw threads extending radially inward from the interior sidewall toward a center longitudinal axis, wherein the discontinuous threaded portion defines a threadless channel extending along a height of the discontinuous threaded portion, a first threadless channel interior sidewall having: a first threadless channel edge disposed radially outward from and circularly adjacent to a first edge of the interior sidewall to define a first step disposed radially between the first edge of the interior sidewall and the first threadless channel edge, and a second threadless channel edge disposed radially outward from and circularly adjacent to a second edge of the interior sidewall to define a second step disposed radially between the second edge of the interior sidewall and the second threadless channel edge, wherein the screw threads terminate at or before the first step and the second step, and wherein the first step, the second step, and the threadless channel interior sidewall define a first keyed slot extending longitudinally along the orthopedic instrument, a second threadless channel interior sidewall having: a third threadless channel edge disposed radially outward from and circularly adjacent to a third edge of the interior sidewall to define a third step disposed radially between the third edge of the interior sidewall and the third threadless channel edge, and a fourth threadless channel edge disposed radially outward from and circularly adjacent to a fourth edge of the interior sidewall to define a fourth step disposed radially between the fourth edge of the interior sidewall and the fourth threadless channel edge, wherein the screw threads terminate at or before the third step and the fourth step, wherein the third step, the fourth step, and the second threadless channel interior sidewall define a second keyed slot extending longitudinally along the orthopedic instrument, and wherein the keyed slot is configured to closely receive the interrupted threaded portion of the adaptor.

An exemplary orthopedic medical device connection mechanism comprises: a first medical device having: a protrusion, the protrusion including a proximal end and a distal end distally disposed from the proximal end along a height of a protrusion body, the protrusion body comprising an interrupted threaded portion disposed closer to the distal end than the proximal end; and a second medical device having: a body, an interior sidewall, the interior sidewall defining a hole extending into the body, a discontinuous threaded portion disposed within the hole, the discontinuous threaded portion defining a threadless channel extending along a discontinuous threaded portion height, and the discontinuous threaded portion configured to receive the interrupted threaded portion of the protrusion of the first medical device through the threadless channel.

An exemplary orthopedic medical device connection mechanism can have a protrusion that further comprises a shank portion disposed closer to the proximal end of the protrusion than the distal end.

An exemplary orthopedic medical device connection mechanism can have threads of the interrupted threaded portion and threads of the discontinuous threaded portion having a trapezoidal cross-sectional shape.

An exemplary orthopedic medical device connection mechanism can have the discontinuous threaded portion defining multiple threadless channels extending along the discontinuous threaded portion height. Such an exemplary embodiment may optionally have the discontinuous threaded portion configured to receive the interrupted threaded portion of the protrusion of the first medical device through multiple threadless channels.

An exemplary orthopedic medical device connection mechanism can have threads of the interrupted threaded portion and threads of the discontinuous threaded portion that are timed threads.

An exemplary orthopedic medical device connection mechanism can have the first medical device further comprising a base, wherein the protrusion extends from a distal side of the base, and wherein a moveable non-rigid non-ridged spacer extends from the distal side of the base. Such an exemplary embodiment may optionally further comprise a pin extending from the distal side of the base. It will be appreciated that such an exemplary medical device connection mechanism may have the second medical device further comprising a proximal side of the second medical device, wherein the proximal side of the second medical device further comprises a moveable non-rigid non-ridged spacer receiver. In such and exemplary embodiment, the proximal side of the second medical device may optionally further define an arcuate groove configured to closely receive the pin of the first medical device as a configuration of the medical device connection mechanism changes from a pre-assembled configuration to an assembled configuration.

An exemplary orthopedic medical device connection mechanism can further comprise multiple additional medical devices disposed between the first medical device and the second medical device when the medical device connection mechanism is placed in an assembled configuration.

An exemplary orthopedic medical device connection mechanism can have the first medical device be selected from the group consisting essentially of: an adaptor, a handle, and a positioning member.

An exemplary orthopedic medical device connection mechanism can have the second medical device be selected from the group consisted essentially of: a broach, a reamer, a rasp, a keel punch, and a bone cutting device.

An exemplary orthopedic medical device connection mechanism can have the second medical device be selected from the group consisting essentially of: an endoprosthetic cone, an endoprosthetic implant, and an endoprosthetic implant component.

An exemplary orthopedic medical device connection mechanism can have the second medical device be a secondary adaptor configured to engage an orthopedic instrument, an orthopedic endoprosthetic implant, of a component thereof.

An exemplary orthopedic medical device connection mechanism can have the threadless channel be a keyed slot, the keyed slot being recessed within the body of the second medical device.

An exemplary orthopedic medical device connection mechanism can have the interrupted threaded portion of the protrusion be a keyed interrupted threaded portion.

An exemplary orthopedic medical device connection mechanism comprises: a first medical device having: a protrusion, the protrusion including a proximal end and a distal end distally disposed from the proximal end along a height of a protrusion body, the protrusion body comprising an interrupted threaded portion disposed closer to the distal end than the proximal end; and a second medical device having: a body, an interior sidewall, the interior sidewall defining a hole extending into the body, a discontinuous threaded portion disposed within the hole, the discontinuous threaded portion defining a threadless channel extending along a discontinuous threaded portion height, and the discontinuous threaded portion configured to receive the interrupted threaded portion of the protrusion of the first medical device through the threadless channel, wherein threads of the interrupted threaded portion and threads of the discontinuous threaded portion are timed threads.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. An orthopedic medical device connection mechanism comprising:

a first medical device having:

a protrusion, the protrusion including a proximal end and a distal end distally disposed from the proximal end along a height of a protrusion body, the protrusion body comprising an interrupted threaded portion disposed closer to the distal end than the proximal end; and a second medical device having:

a body, an interior sidewall, the interior sidewall defining a hole extending into the body, the interior sidewall providing a continuously perimeter around the hole, wherein the interior sidewall has a substantially uniform height for the continuous perimeter of the hole, a discontinuous threaded portion disposed within the hole on an interior discontinuous threaded sidewall portion of the interior sidewall, the discontinuous threaded portion defining a threadless channel on a threadless channel interior sidewall portion of the interior sidewall defining the hole, the discontinuous threaded portion extending along a discontinuous threaded portion height, and the discontinuous threaded portion configured to receive the interrupted threaded portion of the protrusion of the first medical device through the threadless channel.

2. The orthopedic medical device connection mechanism of claim 1, wherein the protrusion further comprises a shank portion disposed closer to the proximal end of the protrusion than the distal end.

3. The orthopedic medical device connection mechanism of claim 1, wherein threads of the interrupted threaded portion and threads of the discontinuous threaded portion have a trapezoidal cross-sectional shape.

4. The orthopedic medical device connection mechanism of claim 1, wherein the discontinuous threaded portion defines multiple threadless channels extending along the discontinuous threaded portion height.

5. The orthopedic medical device connection mechanism of claim 4, wherein the discontinuous threaded portion is configured to receive the interrupted threaded portion of the protrusion of the first medical device through multiple threadless channels.

6. The orthopedic medical device connection mechanism of claim 1, wherein threads of the interrupted threaded portion and threads of the discontinuous threaded portion are timed threads.

7. The orthopedic medical device connection mechanism of claim 1, wherein the first medical device further comprises a base, the protrusion extends from a distal side of the base, and a moveable spacer extends from the distal side of the base.

8. The orthopedic medical device connection mechanism of claim 7 further comprising a pin extending from the distal side of the base.

9. The orthopedic medical device connection mechanism of claim 8, wherein the second medical device further comprises a proximal side of the second medical device, wherein the proximal side of the second medical device further comprises a moveable spacer receiver.

10. The orthopedic medical device connection mechanism of claim 9, wherein the proximal side of the second medical device further defines an arcuate groove configured to closely receive the pin of the first medical device as a configuration of the medical device connection mechanism changes from a preassembled configuration to an assembled configuration.

11. The orthopedic medical device connection mechanism of claim 1, wherein the first medical device is selected from the group consisting essentially of: an adaptor, a handle, and a positioning member.

12. The orthopedic medical device connection mechanism of claim 1, wherein the second medical device is selected from the group consisted essentially of: a broach, a reamer, a rasp, a keel punch, and a bone cutting device.

13. The orthopedic medical device connection mechanism of claim 1, wherein the second medical device is selected from the group consisting essentially of: an endoprosthetic cone, an endoprosthetic implant, and an endoprosthetic implant component.

14. The orthopedic medical device connection mechanism of claim 1, wherein the second medical device is a secondary adaptor configured to engage an orthopedic instrument, an orthopedic endoprosthetic implant, of a component thereof.

15. The orthopedic medical device connection mechanism of claim 1, wherein the threadless channel is a keyed slot, the keyed slot being recessed within the body of the second medical device.

16. The orthopedic medical device connection mechanism of claim 1, wherein the interrupted threaded portion of the protrusion is a keyed interrupted threaded portion.

17. An orthopedic medical device connection mechanism comprising:

a first medical device having:

a protrusion, the protrusion including a proximal end and a distal end distally disposed from the proximal end along a height of a protrusion body, the protrusion body comprising an interrupted threaded portion disposed closer to the distal end than the proximal end; and a second medical device having:

a body, an interior sidewall, the interior sidewall defining a hole extending into the body, the interior sidewall providing a continuously perimeter around the hole, wherein the interior sidewall has a substantially uniform height for the continuous perimeter of the hole, and a discontinuous threaded portion disposed within the hole on an interior discontinuous threaded sidewall portion of the interior sidewall, the discontinuous threaded portion defining a threadless channel on a threadless channel interior sidewall portion of the interior sidewall defining the hole, the discontinuous threaded portion extending along a discontinuous threaded portion height, and the discontinuous threaded portion configured to receive the interrupted threaded portion of the protrusion of the first medical device through the threadless channel, wherein threads of the interrupted threaded portion and threads of the discontinuous threaded portion are timed threads.

18. The orthopedic medical device connection mechanism of claim 17, wherein a step is present between the interior discontinuous threaded sidewall portion of the interior sidewall and the threadless channel interior sidewall portion of the interior sidewall.

19. The orthopedic medical device connection mechanism of claim 1, wherein a step is present between the interior discontinuous threaded sidewall portion of the interior sidewall and the threadless channel interior sidewall portion of the interior sidewall.

20. The orthopedic medical device connection mechanism of claim 1, wherein the interior sidewall includes at least one groove on a proximal side of the second medical device.

* * * * *